(12) United States Patent
Dahmani

(10) Patent No.: US 11,160,929 B2
(45) Date of Patent: Nov. 2, 2021

(54) AUTO-INJECTOR DEVICE WITH INTERCHANGEABLE MODULES FOR DIMENSIONAL AND OPERATIONAL COMPATIBILITY WITH A VARIETY OF DIVERSE PRE-FILLED CARTRIDGES

(71) Applicant: QuiO Technologies LLC, Chicago, IL (US)

(72) Inventor: Alexander Dahmani, New York, NY (US)

(73) Assignee: QuiO Technologies LLC, New York, NY (US)

( * ) Notice: Subject to any disclaimer, the term of this patent is extended or adjusted under 35 U.S.C. 154(b) by 399 days.

(21) Appl. No.: 15/739,794

(22) PCT Filed: Jun. 27, 2016

(86) PCT No.: PCT/US2016/039529
§ 371 (c)(1),
(2) Date: Dec. 26, 2017

(87) PCT Pub. No.: WO2016/210404
PCT Pub. Date: Dec. 29, 2016

(65) Prior Publication Data
US 2018/0193564 A1    Jul. 12, 2018

Related U.S. Application Data

(60) Provisional application No. 62/185,012, filed on Jun. 26, 2015.

(51) Int. Cl.
*A61M 5/24* (2006.01)
*A61M 5/20* (2006.01)
(Continued)

(52) U.S. Cl.
CPC ............... *A61M 5/24* (2013.01); *A61M 5/20* (2013.01); *A61M 5/31* (2013.01); *A61M 5/315* (2013.01);
(Continued)

(58) Field of Classification Search
CPC ............ A61M 5/24; A61M 5/20; A61M 5/31; A61M 5/315; A61M 5/32; A61M 5/46;
(Continued)

(56) References Cited

U.S. PATENT DOCUMENTS

| 5,354,287 A | 10/1994 | Wacks | |
|---|---|---|---|
| 2004/0210199 A1* | 10/2004 | Atterbury | G01D 5/25 604/224 |

(Continued)

FOREIGN PATENT DOCUMENTS

| WO | WO2005/077441 | 8/2005 |
|---|---|---|
| WO | WO2009/143255 | 11/2009 |

(Continued)

OTHER PUBLICATIONS

Supplementary European Search Report dated Nov. 27, 2018 for European Application No. 16815479.7.
(Continued)

*Primary Examiner* — Nathan R Price
*Assistant Examiner* — Courtney B Fredrickson
(74) *Attorney, Agent, or Firm* — Perkins Coie LLP

(57) ABSTRACT

Auto-injectors and associated assemblies and methods for delivery of medicament in a controlled manner are disclosed herein.

12 Claims, 17 Drawing Sheets

(51) Int. Cl.
*A61M 5/315* (2006.01)
*A61M 5/50* (2006.01)
*A61M 5/32* (2006.01)
*A61M 5/31* (2006.01)
*A61M 5/46* (2006.01)
*G16H 20/17* (2018.01)

(52) U.S. Cl.
CPC ............... *A61M 5/32* (2013.01); *A61M 5/322* (2013.01); *A61M 5/46* (2013.01); *A61M 5/50* (2013.01); *A61M 5/326* (2013.01); *A61M 2005/206* (2013.01); *A61M 2005/2013* (2013.01); *A61M 2005/31588* (2013.01); *A61M 2205/13* (2013.01); *A61M 2205/50* (2013.01); *A61M 2205/60* (2013.01); *A61M 2205/6018* (2013.01); *A61M 2205/6063* (2013.01); *G16H 20/17* (2018.01)

(58) Field of Classification Search
CPC ................... A61M 5/50; A61M 5/326; A61M 2005/2013; A61M 2005/206; A61M 2005/31588
See application file for complete search history.

(56) References Cited

U.S. PATENT DOCUMENTS

| | | | |
|---|---|---|---|
| 2011/0021905 A1* | 1/2011 | Patrick | A61M 5/1452 600/424 |
| 2014/0012229 A1* | 1/2014 | Bokelman | A61M 5/2033 604/506 |
| 2014/0142507 A1* | 5/2014 | Armes | A61M 5/20 604/112 |

FOREIGN PATENT DOCUMENTS

| | | |
|---|---|---|
| WO | 2012019641 A1 | 2/2012 |
| WO | WO2012/145685 | 10/2012 |
| WO | WO2012/164390 | 12/2012 |
| WO | 2013065055 A1 | 5/2013 |
| WO | WO2014/066256 | 5/2014 |

OTHER PUBLICATIONS

International Search Report and Written Opinion dated Nov. 16, 2016 for International Application No. PCT/US2016/039529.

* cited by examiner

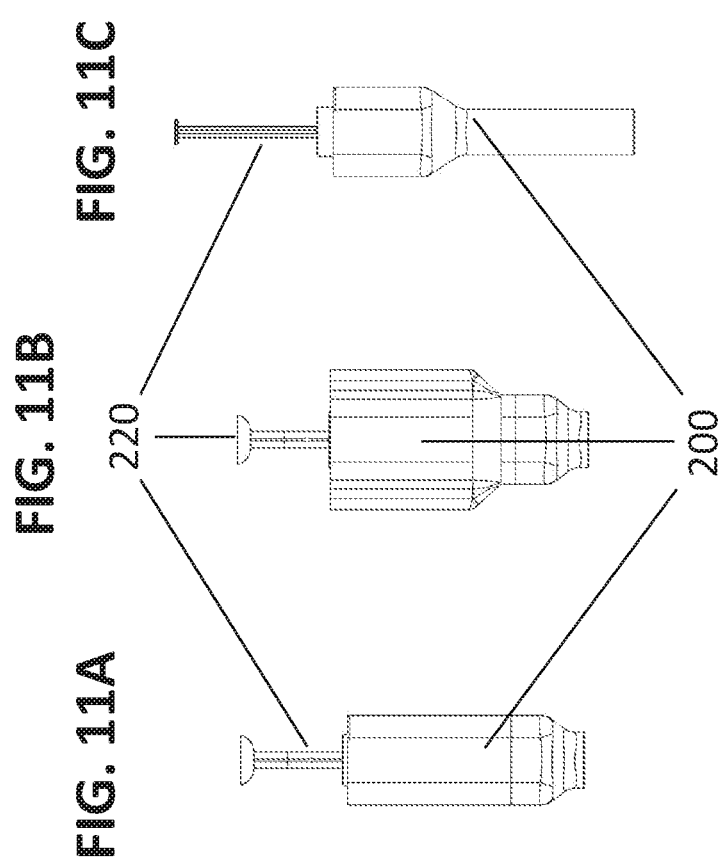

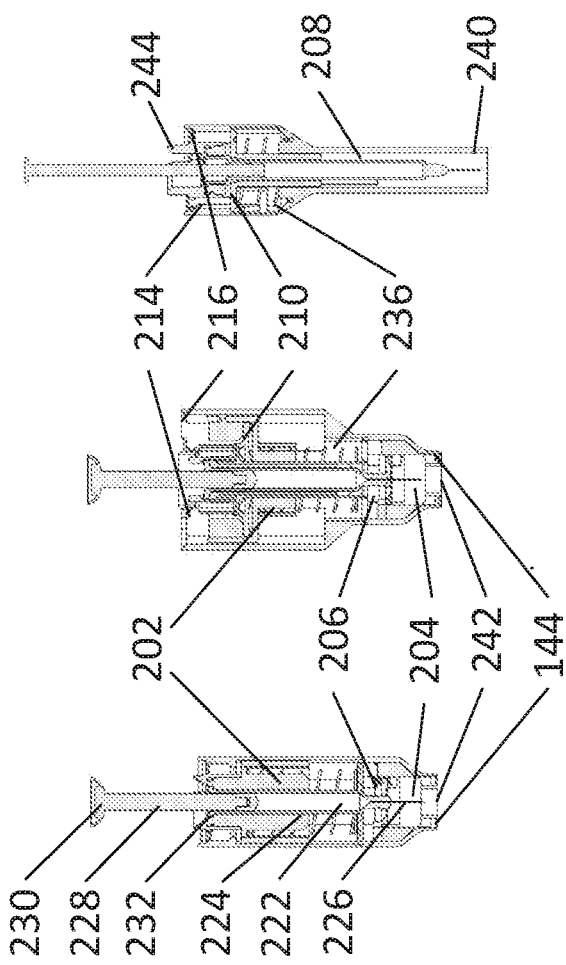

AUTO-INJECTOR DEVICE WITH INTERCHANGEABLE MODULES FOR DIMENSIONAL AND OPERATIONAL COMPATIBILITY WITH A VARIETY OF DIVERSE PRE-FILLED CARTRIDGES

PRIORITY CLAIM

This application is a 371 U.S. National Stage application of International PCT Application No. PCT/US2016/039529, filed Jun. 27, 2016, which claims priority to U.S. Provisional Patent Application Ser. No. 62/185,012 which was filed on Jun. 26, 2015, the entire contents of which are incorporated herein by reference and relied upon.

TECHNICAL FIELD

The present technology relates generally to an automatic injector device ("injector") and associated systems and methods. In particular, several embodiments are directed to an automatic injector device for controlled delivery of a wide variety of drug/cartridge combination products, such as a medicament dosage contained within a pre-filled cartridge.

BACKGROUND

Pre-filled cartridges, such as a syringe, are used for parenteral delivery of medicament solutions (e.g., liquid or cream medicament) such as drug solutions, drug suspensions, vaccines, and other medicinal therapies. Typical pre-filled cartridges include a primary container that houses the drug solution, a hypodermic needle in fluid communication with the primary container, and a piston comprising a plunger head designed to accept an axial force transferred through the plunger rod and received by the syringe stopper located inside the primary container. Such pre-filled cartridges are commercially available from a variety of manufacturers, which through competition has resulted in the proliferation of distinct pre-filled cartridges with diverse form, function and material components. Even within the category of a 1 mL prefilled syringe, the primary container can be long or standard, plastic or glass, the needle length and gauge can vary widely, and safety features can be incorporated, including automatic needle retraction and/or shielding after completion of the injection. In addition to the diversity created by pre-filled cartridge manufacturers, pharmaceutical companies often customize the physical dimensions of these pre-filled cartridges, including the size and shape of components such as flange extenders and plunger heads. The net result is an assortment of distinct combination products (pre-filled cartridge+drug) currently on the market, including similar drugs contained in diverse pre-filled cartridges, as well as one particular type of pre-filled cartridge containing various drug solutions. A robust pipeline of injectable drugs (including biosimilars) and novel pre-filled cartridges promises to increase the range and diversity of combination products marketed in the future.

Auto-injectors use an automatic mechanism (e.g., an electrically powered drive unit) to insert a hypodermic needle through the skin of the patient and into the underlying tissue for delivery of the drug. Conveniently, auto-injectors can be operated by non-medical users for the subcutaneous administration of a drug or by patients for self-administration. However, the majority of auto-injectors are disposable, spring-driven devices that are suitable for the injected delivery of only one specific drug contained in a particular type of pre-filled cartridge. This is partly due to the unique physical qualities inherent to each injectable drug, including viscosity, which affects the automatic injection process, such as the force required to displace the drug solution. The required injection force is also dependent on multiple components of the pre-filled cartridge, including needle length and gauge, primary container size, material of each component, etc. Even more advanced electromechanical auto-injectors that have been developed are still limited to the injected delivery of one drug or one type of pre-filled cartridge. The drug and pre-filled cartridge variables that affect the injection process have been well characterized to-date, and are used by auto-injector manufacturers when designing and optimizing a particular auto-injector device for a specific pre-filled cartridge/drug combination product. Historically, great cost and effort has been required in commercializing an existing auto-injector for a new cartridge/drug combination product, which has limited the pace of improvement and thus, the benefits realized by the patients operating them.

SUMMARY

Methods and materials are provided for the administration of a medicament to a subject.

The present disclosure provides an injector assembly for automatically delivering a dose of a medicament to a subject, the injector assembly comprising:
an activation switch for initiating automatic delivery of the dose of the medicament;
a needle aperture at a distal end of the injector assembly configured for a needle to pass therethrough;
a plunger drive mechanism for applying pressure to a plunger assembly, the plunger drive mechanism including a motor operably connected to the activation switch, and an actuator operably connected to the motor and the plunger assembly;
a surface for operatively connecting to at least a portion of a removable cartridge module, the removable cartridge module including:
a needle housing for dictating a range of injection depths possible;
a plunger housing for aligning the plunger assembly with the plunger drive mechanism;
an identification element containing a code associated with a pre-filled cartridge and/or medicament contained within, and
a cavity for reversibly securing the pre-filled cartridge;
at least one engagement feature for securing the removable cartridge module to the surface; and
a cartridge drive assembly for moving the pre-filled cartridge axially between the proximal and distal end of the injector assembly, the cartridge drive assembly including at least one gear element operably connected to the motor and the activation switch.

The present disclosure provides an injector assembly for automatically delivering a dose of a medicament to a subject, the injector assembly comprising:
an activation switch for initiating automatic delivery of the dose of the medicament;
a needle aperture at a distal end of the injector assembly configured for a needle to pass therethrough;
a plunger drive mechanism for applying pressure to a plunger assembly, the plunger drive mechanism including a motor operably connected to the activation switch, and an actuator operably connected to the motor and the plunger assembly;

a surface for operatively connecting to at least a portion of a removable cartridge module, the removable cartridge module including:
  a needle housing for dictating a range of injection depths possible;
  a plunger housing for aligning the plunger assembly with the plunger drive mechanism;
  an identification element containing a code associated with a pre-filled cartridge and/or medicament contained within, and
  a cavity for reversibly securing the pre-filled cartridge; and
at least one engagement feature for securing the removable cartridge module to the surface.

In some embodiments, the injector assembly further comprises an identification reader for reading an identification element containing the code of the cartridge module.

In some embodiments, the injector assembly further comprises a code reader for reading a label of the pre-filled cartridge.

In some embodiments, the injector assembly further comprises at least one sensor. In some embodiments, the at least one sensor is a pressure sensor. In other embodiments, the at least one sensor is a skin sensor.

In some embodiments, the injector assembly further comprises a battery operably connected to the control unit.

In some embodiments, the removable cartridge module includes a top portion integrated with a door.

In some embodiments, the injector assembly is configured to prevent activation of the cartridge drive assembly and/or the plunger drive assembly if the sensor does not detect a surface of the subject (e.g., skin) when the activation switch is pressed.

In some embodiments, the removable cartridge module further includes a feature conforming to a flange of the pre-filled cartridge.

In some embodiments, wherein upon activation of the activation switch and detection of patient contact by the sensor, the cartridge drive assembly moves the cartridge module a first pre-determined distance towards the distal end of the injector assembly and optionally thereafter moves the cartridge away from the distal end of the injector assembly by at least the first pre-determined distance. In some embodiments, the first pre-determined distance is associated with the identification code. In other embodiments, wherein upon activation of the activation switch, detection of patient contact by the sensor, and movement of the cartridge drive assembly to a first pre-determined distance towards the distal end of the injector, the plunger drive mechanism moves the plunger a second pre-determined distance towards the distal end of the injector assembly. In some embodiments, the second pre-determined distance is associated with the identification code.

In some embodiments, a barrel of the pre-filled cartridge includes the medicament in an amount of at least 1 dose. In other embodiments, a barrel of the pre-filled cartridge includes the medicament in an amount of at least 2 doses, at least 3 doses, at least 4 doses, at least 5 doses, at least 6 doses, at least 7 doses, at least 8 doses, at least 9 doses, at least 10 doses, at least 11 doses, at least 12 doses, at least 13 doses, at least 14 doses, at least 15 doses, at least 16 doses, at least 17 doses, at least 18 doses, at least 19 doses, at least 20 doses, or more than 20 doses.

In some embodiments, the injector assembly further comprises a control system including a microcontroller configured to:

store a plurality of identification codes;
  store a library of injection programs associated with at least one identification code, the injection program comprises at least: a first and/or a second pre-determined distance associated with each identification code, and a pre-determined injection force associated with each identification code;
  process inputs received from sensors and from the patient; and/or
  execute an appropriate injection program using inputs from sensors and/or patient.

In some embodiments, the control system further comprises a transceiver for receiving data associated with identification codes and injection programs from a server and/or for sending data associated with the performance of an injection, including at least one of:
  the identification code of the operatively connected cartridge module;
  the injection program executed;
  the temperature of the pre-filled cartridge at the time of the injection;
  the performance of the motor during injection, including motor speed;
  the duration of time it takes the plunger drive mechanism to move a plunger assembly the second pre-determined distance; and
  any starts or stops after the initiation of the injection.

In some embodiments, the microcontroller is further configured to cause the cartridge drive assembly to move the cartridge the first pre-determined distance towards and away from the distal end of the injector.

In some embodiments, the microcontroller is further configured to cause the plunger drive mechanism to move the plunger the second pre-determined distance by exerting a pre-determined injection force on the plunger.

In some embodiments, the activation switch comprises a button, toggle, lever, dial, or rocker.

In some embodiments, the injector assembly further comprises a spring configured to increase delivery force to the plunger drive mechanism, the spring operably connected to at least a portion of the actuator.

In some embodiments, the surface has features that form functional connections with corresponding fittings on the removable cartridge module when operatively connected to the cartridge module, the functional connections being configured to: centrally align an internal cavity of the cartridge module with the plunger drive mechanism of the injector assembly; operably mate the cartridge module to the cartridge drive mechanism of the injector assembly; operably mate the electronic components of the cartridge module with the control system of the injector assembly; and/or operably mate the identification element with the identification reader of the injector assembly.

In some embodiments, an operative connection with the removable cartridge module is only formed when the at least one engagement feature securely attaches to at least one fitting of the cartridge module.

In some embodiments, the injector assembly further comprises a display for reporting information and/or instructions to the subject. In other embodiments, the injector assembly further comprises at least one indicator (e.g., a light, a vibration, or a sound) configured to provide information and/or instruction to the subject.

In some embodiments, the injector assembly further comprises a cartridge drive assembly for moving the pre-filled cartridge axially between the proximal and distal end of the injector assembly, the cartridge drive assembly including at least one gear element operably connected to the motor and the activation switch the injector assembly is configured to stop activation of the cartridge drive assembly and/or the plunger drive assembly if the sensor stops detecting a surface of the subject (e.g., skin) after the activation switch is pressed. The present disclosure provides cartridge modules comprising: a needle housing for dictating a range of injection depths possible; a plunger housing for aligning a plunger assembly with a plunger drive mechanism; a cavity for reversibly securing a cartridge pre-filled with a medicament; an identification element containing a code associated with a pre-filled cartridge and/or medicament contained within; at least one fitting for removably engaging the cartridge module in an injector assembly; and at least one fitting for operably mating the cartridge module with a cartridge drive assembly, optionally wherein the cartridge drive assembly is integrated with the injector assembly.

In some embodiments, the cartridge module further comprises at least one fitting for operably mating electronic components with a control system, optionally wherein the control system is integrated with the injector assembly.

In some embodiments, the cartridge module further comprises a shoulder support for mating with a pre-filled cartridge. In other embodiments, the cartridge module further comprises a flange support for mating with a pre-filled cartridge. In some embodiments, the shoulder support and/or the flange support are configured to prevent mating with an undesired pre-filled cartridge.

In some embodiments, the cartridge module comprises a cavity that includes a barrel housing between shoulder support and flange support, optionally configured to prevent mating with an undesired pre-filled cartridge.

In some embodiments, the needle housing is configured to prevent mating with an undesired pre-filled cartridge. In other embodiments, the needle housing is configured to align or mate with a needle aperture of an injector device.

In some embodiments, the cavity is centrally aligned with the plunger drive mechanism of an injector device when the fittings are properly engaged with the injector device.

In some embodiments, the identification element is only in communication with a cartridge module identification reader when the fittings are properly engaged with an injector device.

In some embodiments, the cartridge module further comprises a heating element.

In some embodiments, the cartridge module is configured to facilitate different functions based on the identification element, for example, recordation of medicament temperature, heating of medicament to a specific temperature, wireless communication with a server, and removal of a cartridge needle cap.

The present disclosure provides methods of administering a medicament to a subject, the method comprising: providing an injector assembly to the subject; and providing instructions to the subject for administering a medicament using the injector assembly, wherein the injector assembly is configured to cause a needle to penetrate skin of the subject and thereafter inject an amount of the medicament to the subject through the needle.

The present disclosure also provides methods of administering a medicament to a subject, the method comprising: providing a cartridge module to the subject; and providing instructions to the subject for administering the medicament using the cartridge module, wherein the cartridge module is configured to removably mate with an injector assembly, the injector assembly is configured to cause a needle to penetrate skin of the subject and thereafter inject an amount of the medicament to the subject through the needle.

The present disclosure further provides methods of administering a medicament to a subject, the method comprising: providing a pre-filled cartridge to the subject; and providing instructions to the subject for administering the medicament using the pre-filled cartridge, wherein the pre-filled cartridge includes a medicament and is configured to mate with a cartridge module removably and operatively connected to an injector assembly, the injector assembly configured to cause a needle to penetrate skin of the subject and thereafter inject an amount of the medicament to the subject through the needle.

In some embodiments, the methods comprise an injector assembly of any of the above embodiments.

In some embodiments, the methods comprise a cartridge module of any of the above embodiments.

In some embodiments, the medicament is in a pre-filled cartridge configured to operably mate with the injector assembly.

In some embodiments, the pre-filled cartridge is housed in a cartridge module, wherein the cartridge module operatively connects to the injector assembly.

In some embodiments, the instructions to the subject comprise information on device status, needle cap status, injection run status, or any combination thereof. In other embodiments, the instructions include information on how to configure one or more attributes of the injector assembly selected from the group consisting of: injection depth, injection speed, injection amount, or any combination thereof.

In some embodiments, the cartridge module is configured to provide proper injection depth and/or injection amount.

In some embodiments, the injection depth, injection speed, and/or the injection amount are associated with an identification code.

In some embodiments, the cartridge module includes the identification code.

In some embodiments, the present disclosure provides an injector assembly for automatically delivering a dose of a medicament to a subject in a controlled manner, the injector assembly comprising an activation switch for initiating automatic delivery of the dose of the medicament; a needle aperture at a distal end of the injector assembly and for enabling an injection needle to pass there through; a plunger drive mechanism for applying pressure to the plunger assembly; an surface for operatively connecting to at least a portion of a removable cartridge module, the removable cartridge module including (a) a needle housing for dictating the range of injection depths or possible, (b) a plunger housing for aligning a plunger assembly with the plunger drive unit, (c) an identification code associated with the medicament, and (d) a cavity for reversibly securing a pre-filled cartridge in the proper orientation.

In one embodiment, the pre-filled cartridge includes: (i) a barrel for containing the medicament and having a proximal end and a distal end, (ii) a needle operably connected to the distal end of the barrel, (iii) a plunger assembly including a plunger rod having a distal end initially located near the proximal end of the barrel, and a proximal end including a plunger head, and (iv) an amount of the medicament.

In one embodiment, the plunger drive mechanism includes a motor operably connected to the activation switch (e.g. a button, toggle, lever, dial, rocker or similar) and an actuator operably connected to the motor and the plunger assembly; at least one engagement feature for securing the removable cartridge module in the proper orientation; a door, at least a portion of which is optionally substantially transparent, for enabling connection and/or removal of the removable cartridge module to/from the injector, as well as loading and/or removal of the pre-filled cartridge to/from the operatively connected cartridge module cavity; a cartridge drive assembly for moving the cartridge axially towards the proximal and distal end of the injector assembly, the cartridge drive assembly including at least one gear element operably connected to the motor and the activation switch; a code reader for reading an identification code associated with the pre-filled cartridge and the medicament contained within the cartridge; a sensor for detecting contact with skin of the subject; a battery operably connected to the motor; a control unit (e.g. microcontroller) with associated memory containing a library of injection programs and operably connected to the sensors, code reader, drive mechanism(s) and activation switch.

In some embodiments, the present disclosure provides a cartridge module comprising a needle housing for dictating the range of injection depths possible; a plunger housing for aligning a plunger assembly with the plunger drive unit; a cavity for reversibly securing a cartridge pre-filled with a medicament; an identification code associated with the pre-filled cartridge and the medicament contained within; at least one fitting for removably engaging the cartridge module with the injector assembly in the proper orientation; and at least one fitting for engaging the cartridge module with a cartridge drive assembly, optionally wherein the cartridge drive assembly is integrated with the injector assembly.

In some embodiments, the present disclosure provides a method of administering a medicament to a subject, the method comprising providing an injector assembly with operatively connected cartridge module to the subject, for example as described herein; and providing instructions to the subject for administering the medicament using the injector assembly, wherein the injector assembly is configured to cause a needle to penetrate skin of the subject and thereafter inject an amount of the medicament to the subject through the needle.

In some embodiments, the present disclosure provides a method of administering a medicament to a subject, the method comprising providing a cartridge module to the subject for example as described herein; and providing instructions to the subject for administering the medicament using the cartridge module, wherein the cartridge module is configured to removably mate with an injector assembly, the injector assembly configured to cause a needle to penetrate skin of the subject and thereafter inject an amount of the medicament to the subject through the needle.

In some embodiments, the present disclosure provides a method of administering a medicament to a subject, the method comprising providing a pre-filled cartridge to the subject; and providing instructions to the subject for administering the medicament using the pre-filled cartridge, wherein the pre-filled cartridge includes the medicament and is configured to mate with a cartridge module operatively connected in the injector assembly, the injector assembly configured to cause a needle to penetrate skin of the subject and thereafter inject an amount of the medicament to the subject through the needle.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. For ease of reference, throughout this disclosure identical reference numbers may be used to identify identical or at least generally similar or analogous components or features.

FIGS. 11A, 11B and 11C are a front view of the cartridge module shown in FIG. 6, as well as two additional cartridge modules, illustrating the standard and custom features of the cartridge modules in accordance with an embodiment of the present technology.

FIGS. 12A, 12B and 12C are a cross-sectional front view of the three distinct cartridge modules shown in FIGS. 11A, 11B and 11C, respectively, illustrating how the standard and custom features of the cartridge module removably secure diverse pre-filled cartridges in accordance with an embodiment of the present technology.

DETAILED DESCRIPTION

Figure 1C:
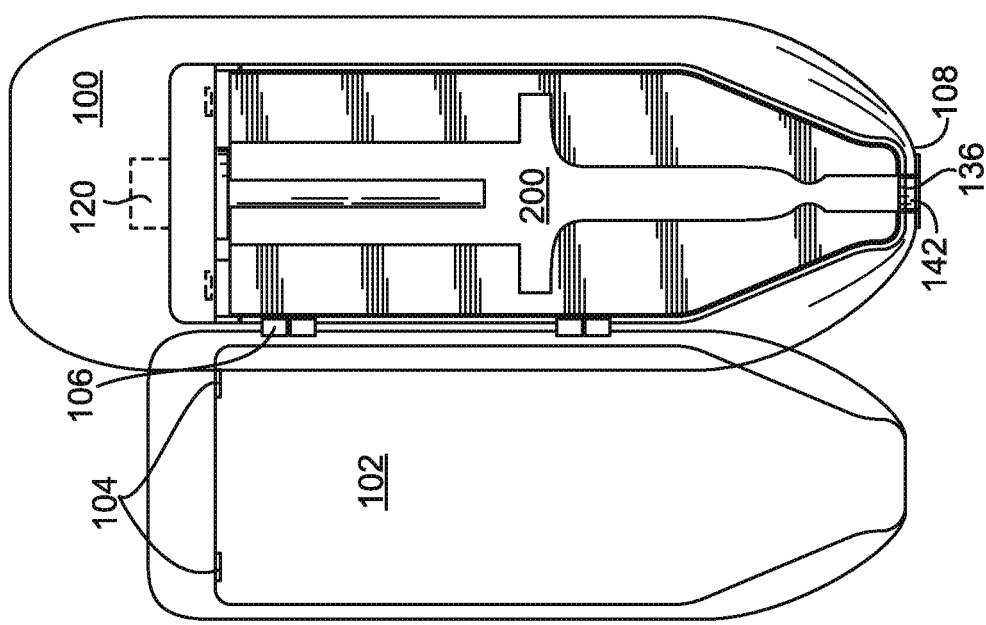
FIGS. 1A, 1B and 1C are a front view of the injector assembly that includes, respectively, an injector with the door closed, an injector with a door open and an injector with a door open and a cartridge module inserted into the injector in accordance with an embodiment of the present technology.

The present technology is directed to apparatuses, systems, and methods for the controlled injection (e.g., parenteral) of medicaments (e.g., liquid or cream) contained in diverse primary containment systems. In particular, embodiments of the present technology relate to electronic injectors and auto-injector assemblies having interchangeable cartridge modules suitable to automatically deliver a predetermined number of dosages (e.g., a single dose volume) of a medicament contained in pre-filled cartridges of various size, shape and functionality. Certain embodiments of the present technology deliver a dose in a controlled manner (within a specified amount of time, at a specified injection depth, at a known drug temperature, etc.) and/or monitor delivery performance of the injector, for example, to determine the identity of the medicament, or to audit the state of the identified medicament as well as the operations of the device itself, before, during and/or after drug delivery.

In certain embodiments, the injector is able to securely house a single cartridge module that is operatively connected prior to distribution. In other embodiments, the cartridge module is operatively connected at the point-of-care and can easily be exchanged for the purpose of delivering pre-filled cartridges of diverse shapes and sizes with one injector. The embodiments related to this technology describe an injector that cooperatively functions with an operatively connected cartridge module to automatically deliver a dose of a medicament contained within a pre-filled cartridge housed in the cavity of the cartridge module. In one embodiment, the steps and functions performed by the injector are independent of the type of cartridge module operatively connected. In other embodiments, the injector is able to detect the cartridge module operatively connected, and utilizes that information to perform functions programmed specifically for the type of cartridge module operatively connected. In further embodiments, the injector is able to detect the cartridge module operatively connected and the combination product loaded into the cartridge module, and utilizes that information to perform functions programmed specifically for the type of combination product loaded into the cartridge module.

In some arrangements, an electronic injector assembly is configured to deliver a single dose of a medicament in a manner that allows for detection and control of various aspects of the delivery process. For example, the injector can detect the identity of the operatively connected cartridge module and use that information to execute the appropriate injection program among a library of injection programs stored in the control unit or an associated memory. In certain embodiments, the injector can detect the temperature of the medicament prior to injection, and display it to the user. In some embodiments, a user can select a rate of injection of the medicament (e.g., within a pre-defined range associated with the cartridge module identity). A rate of injection can be calculated within the context of the use of the injector assemblies described herein. In one embodiment, an injection force for the injection program can be determined based on a number of pre-define variables such as medicament viscosity, volume, syringe barrel and needle dimensions, etc. In some embodiments, a user can enter the identity of their prescribed combination product, which dictates the injection program executed by the injector device.

Specific details of several embodiments of the technology are described below with reference to FIGS. 1A-17. Although many of the embodiments are described below with respect to devices, systems, and methods for controlled automatic injection of medicament into a subject, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1A-17.

Selected Examples of Automatic Injectors and Related Devices

Figure 1B:
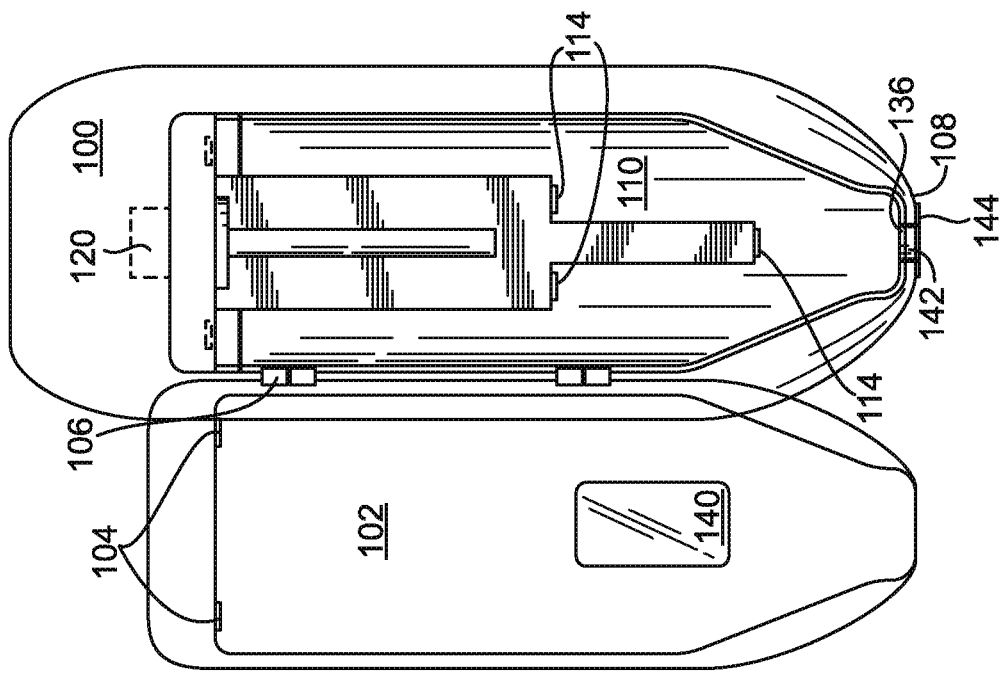
Figure 1A:
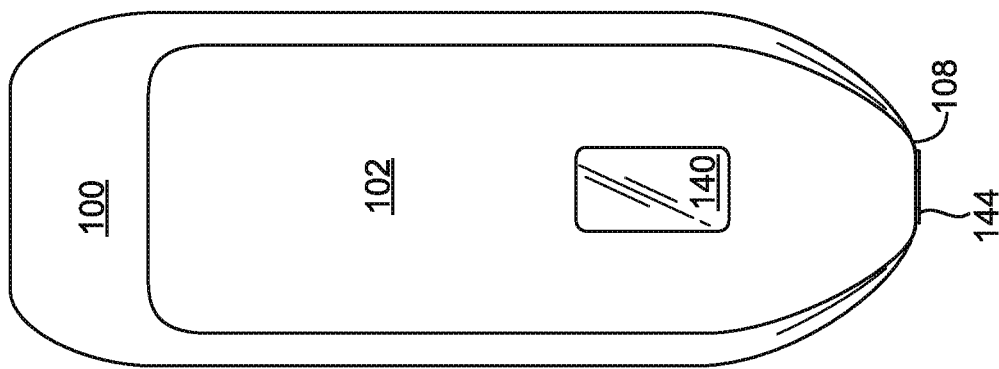

FIGS. 1A, 1B and 1C are a front view of an injector 100 with a door 102 that opens up to the surface of a cartridge module carrier 110 (FIG. 1B) where it can accept a cartridge module 200 (FIG. 1C) in accordance with an embodiment of the present technology. In some embodiments, the door is connected to the injector 100 by a hinge 106 for closable access to the inside of the injector 100. In one embodiment, the door 102 has at least one latch 104 that engages the injector 100 when the door 102 is closed. In some embodiments, the door 102 has a window 140 for viewing a pre-filled cartridge loaded into the device when the door 102 is closed. The injector 100 can operatively connect to a cartridge module 200 through the surface of the cartridge module carrier 110 (FIG. 1C), in order to adapt the injector 100 to accept and deliver a medicament contained within a plurality of diverse pre-filled cartridges.

Figure 2:
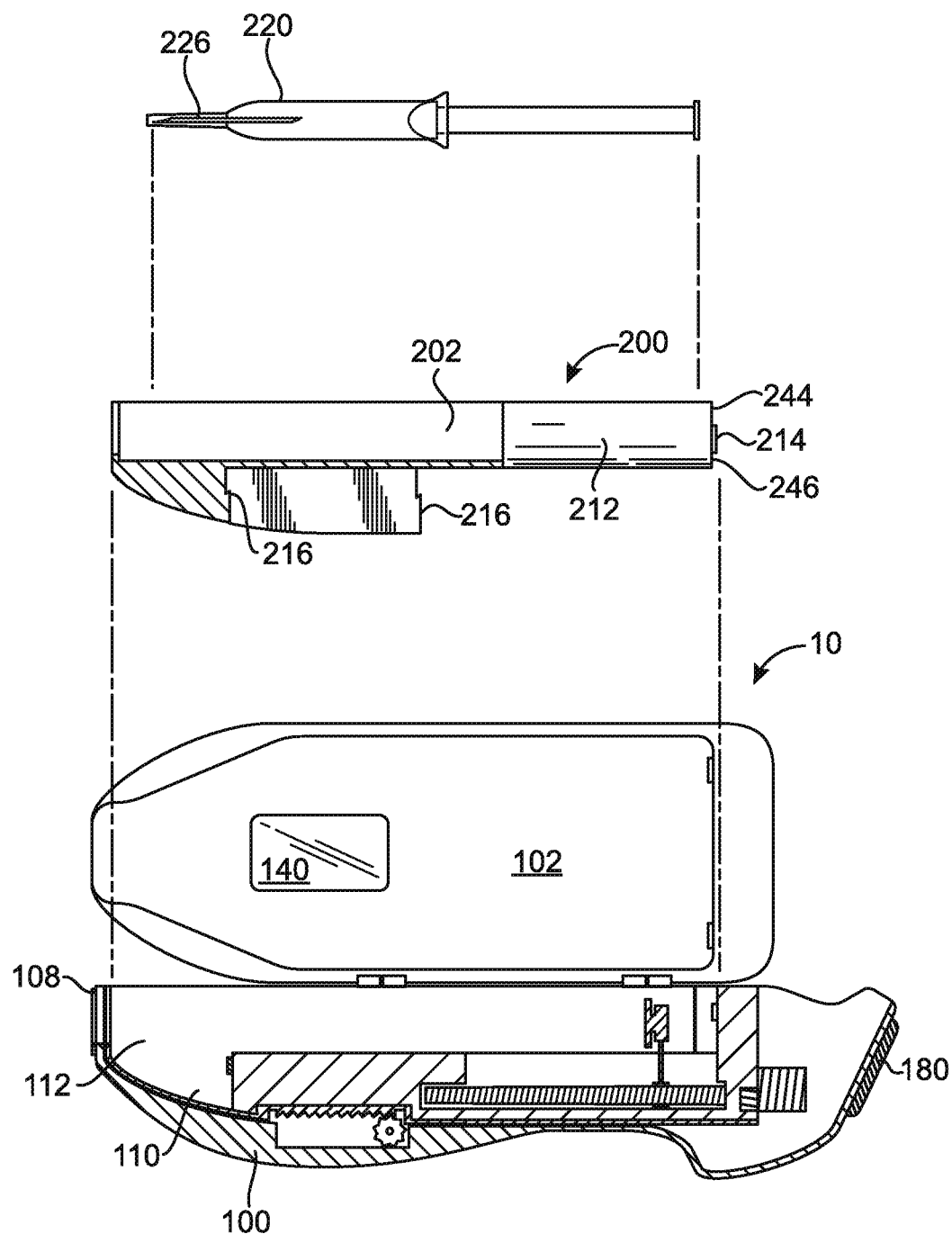
FIG. 2 is a cross-sectional side view of an embodiment of the present technology comprising an automatic injection system, including in descending order, a pre-filled cartridge, the cartridge module shown in FIG. 1C, and the injector shown in FIGS. 1A, 1B and IC, in accordance with an embodiment of the present technology.

FIG. 2 is a cross-sectional side view illustrating the separated components that make up the injector assembly 10 shown in FIG. 1C, including an injector 100 with a cartridge module carrier 110 that houses a cartridge module 200 designed to accept a particular type of pre-filled cartridge 220 in accordance with an embodiment of the present technology. Referring to FIGS. 1A-2 together, and in several embodiments, the injector 100 can be a handheld, reusable auto-injector configured to the accept one of a plurality of cartridge modules 200 through the surface 112 of the cartridge module carrier 110 (FIGS. 1C and 2), and together, the injector assembly 10 delivers a medicament 222 from a pre-filled cartridge 220 contained within the internal cavity 202 of the cartridge module 200 into the tissue of a subject via a hypodermic needle 226 (FIG. 2).

Figure 3A:
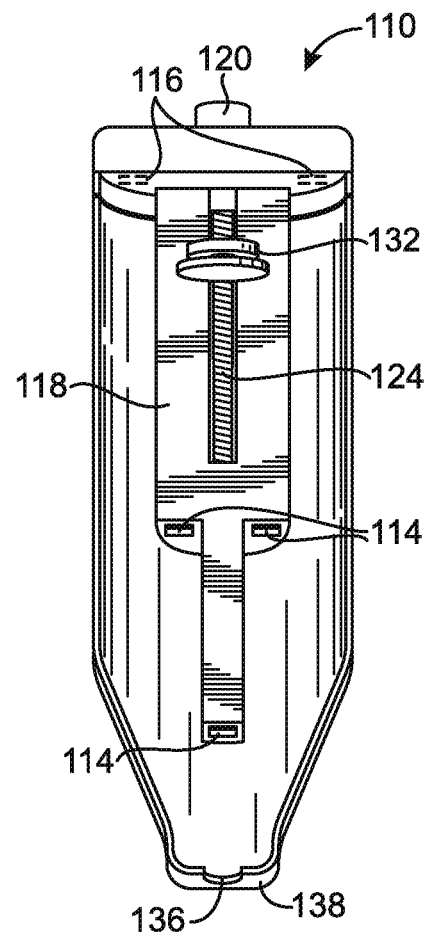
FIGS. 3A and 3B are a front view and cross-sectional side view, respectively, of the cartridge module carrier shown in FIG. 1B, in accordance with an embodiment of the present technology.
Figure 3B:
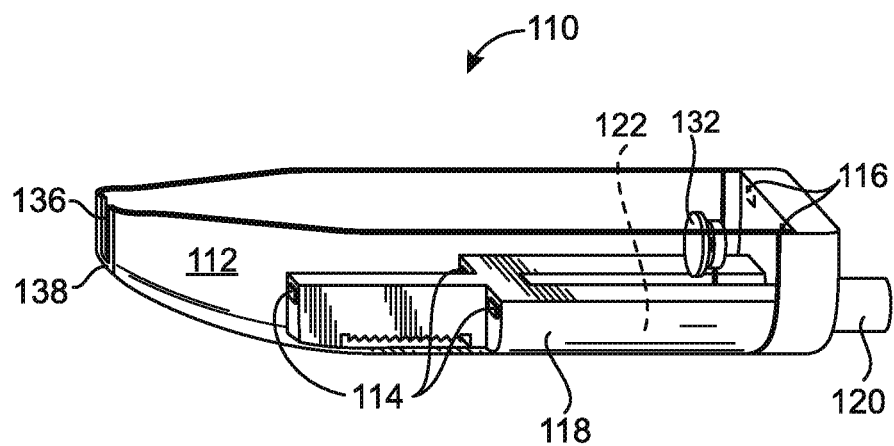

FIGS. 3A and 3B are a front view and cross-sectional side view of the cartridge module carrier 110, respectively. The cartridge module carrier 110 is integral to the injector 100, and facilitates the axial movement of the cartridge module 200 during operation of the injector assembly 10. The cartridge module carrier 110 contains at least one engagement feature 114 responsible for securely engaging one of a plurality of cartridge modules 200. The cartridge module carrier 110 houses a plunger drive mechanism 118 that is operably coupled to a pre-filled cartridge 220 loaded into the cavity 202 of a cartridge module 200. In some embodiments, the plunger drive mechanism 118 is configured to deliver force through a plunger drive unit 132 to impart motion on the plunger assembly 228 of the pre-filled cartridge 220 in order to administer a medicament 222 to a patient. In certain embodiments, the cartridge module carrier 110 has a surface 112 that operatively connects to the cartridge module 200. In such embodiments, the cartridge module carrier 110 has a needle aperture 136 at its distal end 138. In other embodiments, the cartridge module carrier 110 is primarily located beneath the cartridge module 200 forming a base that removably secures the cartridge module 200. In some embodiments, the cartridge module carrier 110 includes a cartridge module identification code reader 116 configured to communicate with the identification element 214 housed within the cartridge module 200, for the purpose of interpreting the identity of the installed cartridge module 200 and communicating it to the control system 150 of the injector 100. For example, the identification element containing the identification code 110 could be a barcode, magnetic tag or RFID tag. In certain embodiments, the identification element is a series of mechanical keys that form a binary code that is read by the cartridge module code reader. In other embodiments, the identification code reader 116 is located apart from the cartridge module carrier 110.

FIGS. 4A, 4B, 4C, 4D, 4E and 4F are a cross-sectional side view of the injector assembly 10 illustrating the positioning of the cartridge module carrier 110 during each progressive step in the injection program, including insertion, injection, and retraction, respectively. FIGS. 4A, 4B, 4C, 4D, 4E and 4F depict a pre-filled cartridge 220 loaded into the injector assembly 10 minus the cartridge module 200. The cartridge module carrier 110 of the injector 100 is operatively coupled to a drive mechanism 134 housed within the injector 100. The cartridge drive mechanism 134 is configured to move the needle 226 of a pre-filled cartridge 220 from a retracted position (FIGS. 4C and 4F) through a needle aperture 142 to an extended position (FIGS. 4A, 4B, 4D and 4E) beyond a distal end 108 of the injector assembly 10 (e.g. for penetrating a subject's skin). After the cartridge drive mechanism 134 has moved the needle 226 to an extended position (FIGS. 4A and 4D), the plunger drive mechanism 118 applies a force to the plunger head 230 in order to inject the medicament 222 into the patient's tissue. Following completion of the injection, the cartridge drive mechanism 134 moves the needle 226 from an extended position (FIGS. 4B and 4E) to a retracted position (FIGS. 4C and 4F), housing the needle 226 inside the injector 100 and protecting the patient from needle-stick injury.

Figure 4A:
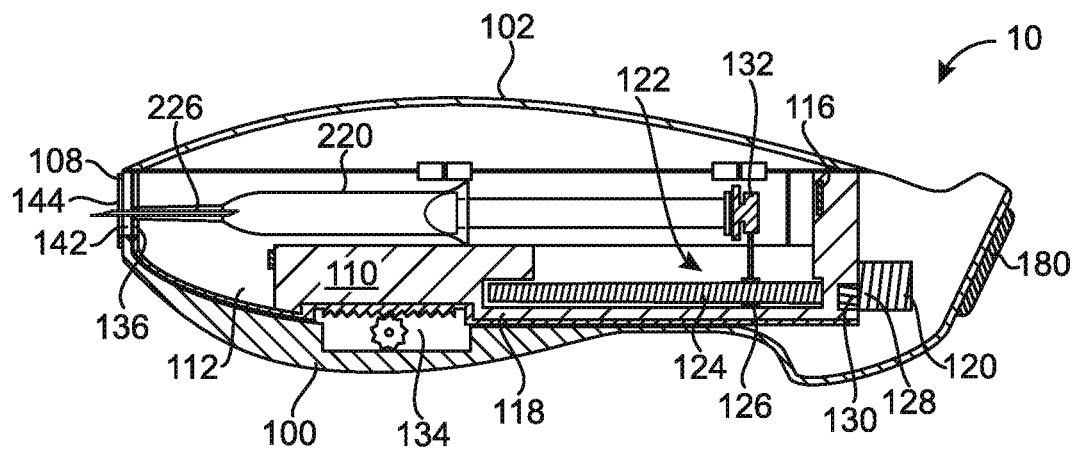
FIGS. 4A, 4B and 4C are a cross-sectional side view of the injector shown in FIGS. 1A, 1B and 1C, in accordance with an embodiment of the present technology.
Figure 4B:
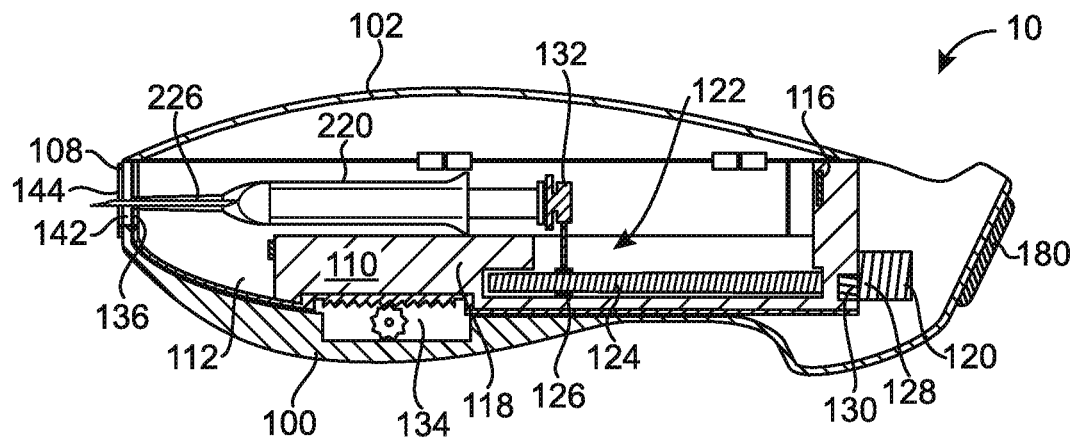
Figure 4C:
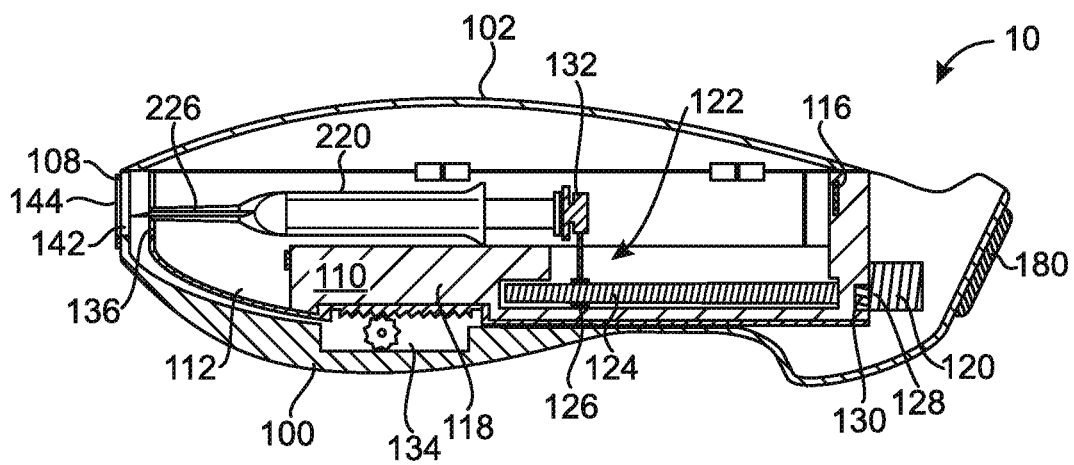

In referring to FIGS. 4A, 4B and 4C the plunger drive mechanism 118 is independent of the cartridge drive mechanism 134. In certain embodiments, the plunger drive mechanism 118 is integral to the cartridge module carrier 110, such that the axial motion imparted by the cartridge drive mechanism 134 moves the cartridge module carrier 110 and its payload, which includes a cartridge module 200 housing a pre-filled cartridge 220, as well as the plunger drive mechanism 118. In certain embodiments, the plunger drive mechanism 118 comprises a motor, such as an electric motor, responsible for generating the force behind the movement of the actuator 122. In some embodiments, the actuator 122 is comprised of a lead nut 126 coupled to a lead screw 124, which is coupled to the output shaft 128 of the motor 120 via a gear set 130. In certain embodiments, the lead nut 126 is connected to the plunger drive unit 132, such that, as the motor 120 drives the rotation of the lead screw 124, the plunger drive unit 132 moves along an axis that runs through the plunger housing 212 of the cartridge module 200 (shown in FIGS. 8B, 9A and 9B). In some embodiments, the plunger drive unit 132 incorporates a compressible spring for smooth transfer of force upon engagement of the plunger head 230. In some embodiments, the plunger drive unit 132 is shaped such that it is capable of engaging a wide variety of plunger heads 230 with distinct shapes and sizes. For example, the plunger drive unit surface facing the plunger assembly could be concave in shape.

Figure 4D:
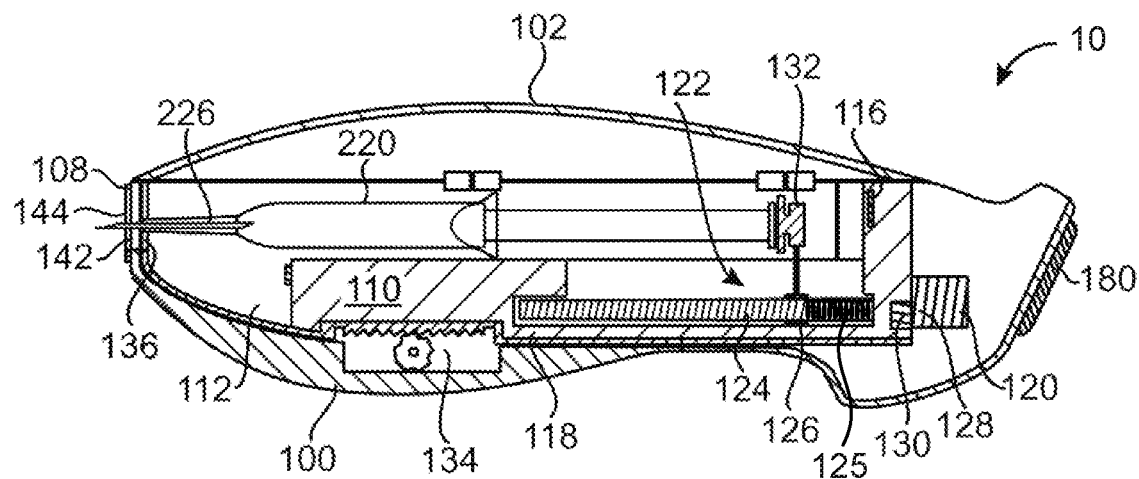
FIGS. 4D, 4E and 4F are a cross-sectional side view of the injector shown in FIGS. 1A, 1B and 1C, in accordance with an embodiment of the present technology.
Figure 4E:
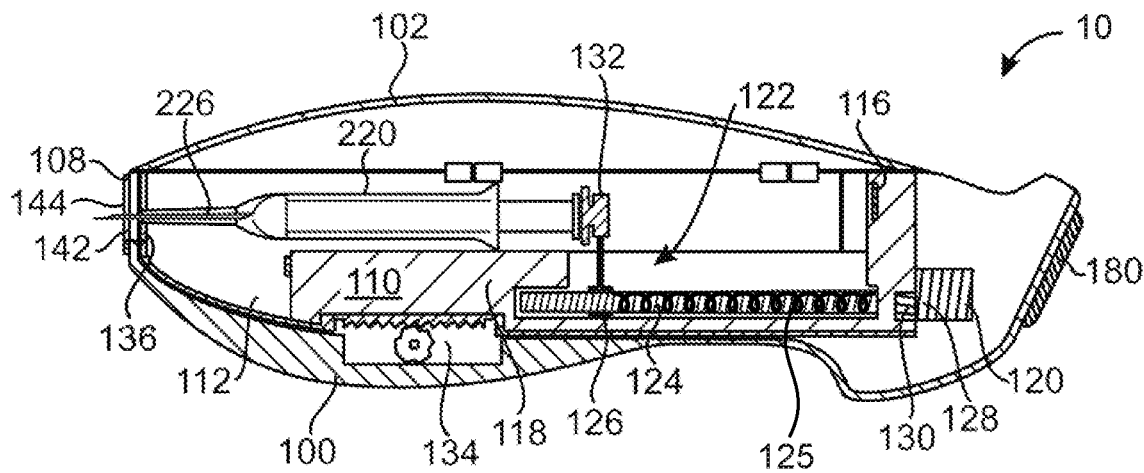
Figure 4F:
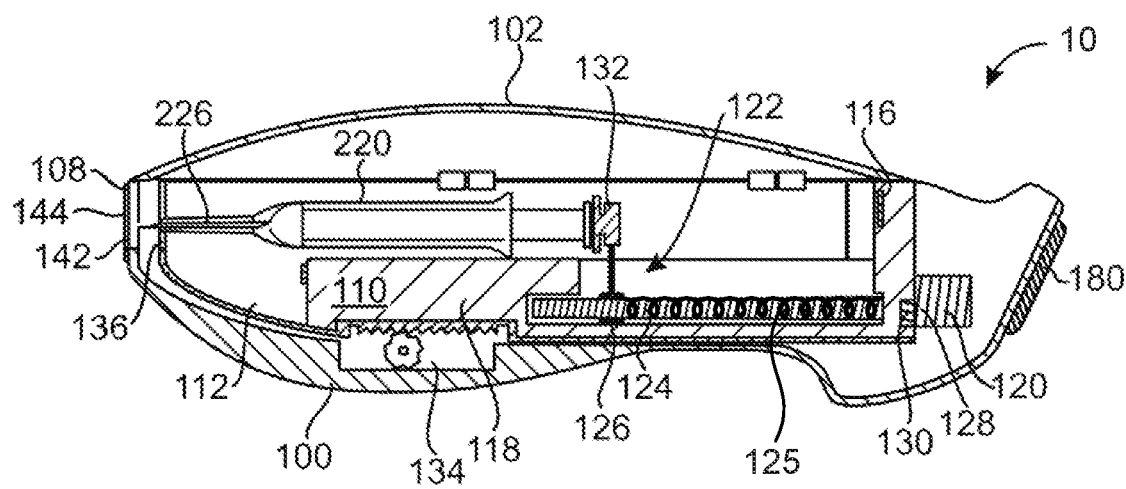

In referring to FIGS. 4D, 4E and 4F the embodiments described above in reference to FIGS. 4A, 4B and 4C apply and an additional element, for example a spring 125, configured to increase delivery force of the drive mechanism is integrated into the injector assembly. The spring 125 can be incorporated around a portion of the lead screw 124. The compression of the spring 125 can be controlled by the movement of the lead screw 124 driven by the motor 120. As the motor 120 moves the lead screw 124, force is delivered to the plunger drive unit 132 by both the spring 125 and the actuator 122. The spring 125 can be weaker than the maximum force delivered by the motor 120, so that upon completion of medicament delivery to a patient, the motor 120 can compress the spring 125 during movement of the lead screw 124 back to a starting position.

Figure 5:
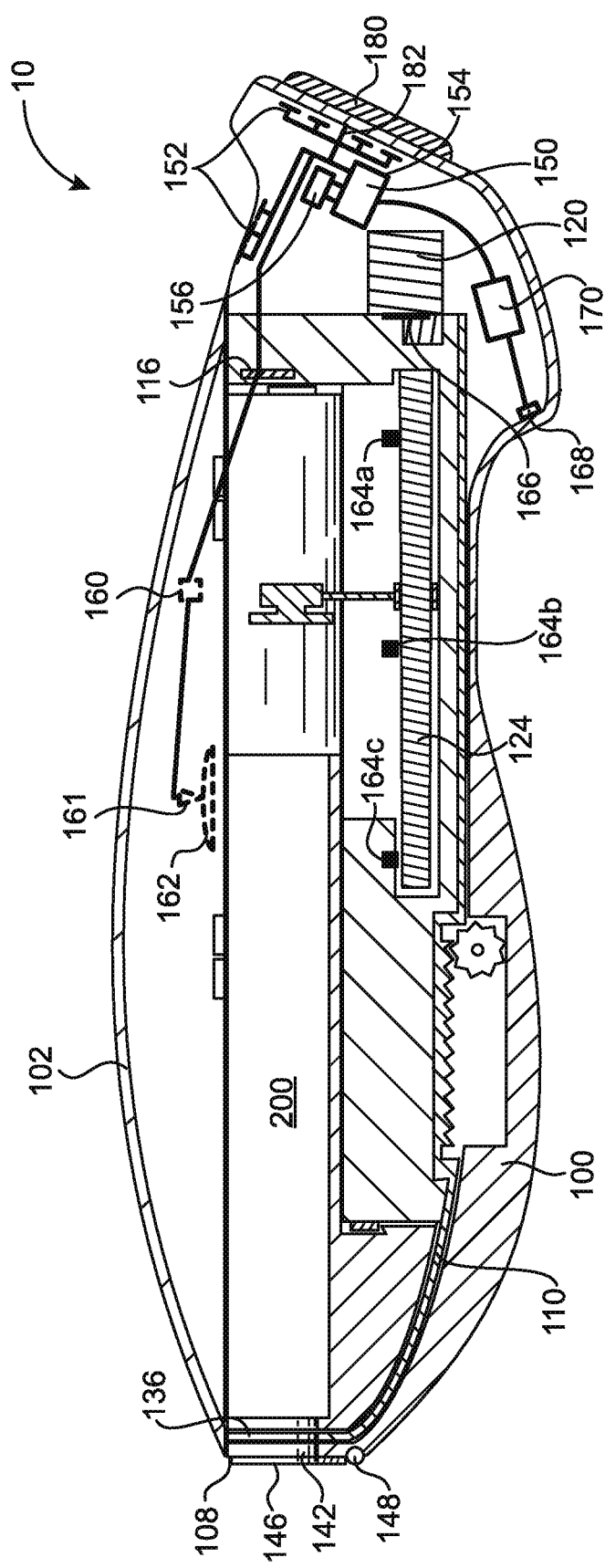
FIG. 5 is a cross-sectional side view of the injector shown in FIGS. 1A, 1B and 1C, illustrating the various components of the electronic control system in accordance with an embodiment of the present technology.

FIG. 5 is a cross-sectional side view of the injector 100 illustrating the various electronic components connected to the control system 150. The control system 150 contains instructions for the automated operations of the injector 100, which can include needle-shield removal, needle insertion, controlled medicament injection, and needle retraction. In certain embodiments, the control system 150 is configured to receive inputs from peripheral sensors and/or user input for the purpose of operating the injector 100. The control system 150 is also connected to a radio transceiver 156, such as a cellular chip, which can wirelessly communicate with a remote server for transmitting and receiving data and firmware applications. In some embodiments, the radio transceiver 156 can communicate with a companion application running on a user's personal electronic device (e.g. smartphone). In certain embodiments, the electronic components of the injector 100 are powered by a battery 170. In one embodiment, the battery 170 is replaceable, such as standard AAA batteries. In further embodiments, the battery 170 is rechargeable through a micro-USB port 168.

In referring to FIG. 5, certain embodiments include a microcontroller 154 is connected to a power source such as a battery 170. In some embodiments, a microcontroller 154 is the central processing component of the control system 150, and is responsible for receiving inputs from a plurality of sensors and distributing commands involved in the operations of the injector 100. In certain embodiments, the control system 150 is connected to receive inputs from peripheral sensors, including a thermal sensor 160. In certain embodiments, the thermal sensor is connected to a thermoresistor circuit 161 and a thermal transducer element 162. In some embodiments, the thermal sensor is located on the internal surface of the door 102 of the injector 100, such that the thermal transducer element 162 is in physical contact with a pre-filled cartridge 220 loaded into the cavity 202 of a cartridge module 200 when the door 102 of the injector 100 is closed. In certain embodiments, the input received from the thermal sensor 160 guides control system 150 in selecting and executing an appropriate injection program. In certain embodiments, the control system 150 is also connected to a cartridge module identification code reader 116 oriented to read a code stored in the identification element 214 of the cartridge module 200. In some embodiments, the cartridge module code reader 116 is integral to the cartridge module carrier 110. In certain embodiments, the control system 150 is connected to patient sensors 144 located at the distal end 108 of the injector 100. In some embodiments, the patient sensors comprise at least two types of sensors, including a pressure sensor 146 and a skin sensor 148. In certain embodiments, inputs received from the patient sensors 144 unlock the activation circuit 182 of the injector 100. In certain embodiments, the control system 150 receives input from the activation circuit 182 connected to the activation switch 180 located on the proximal end of the injector 100. In some embodiments, the control system is connected to the user interface 152. In certain embodiments, the user interface 152 includes LEDs for communicating information to the user such as drug temperature and injection speed settings. In some embodiments, the user interface 152 includes buttons that the user can press for selecting settings related to the operations of the injector 100, such as an injection speed.

In referring to FIGS. 4A-5 together, the control system 150 is connected to at least one drive mechanism, including the plunger drive mechanism 118 and the cartridge drive mechanism 134. In certain embodiments, the plunger drive mechanism 118 comprises a plurality of sensors, including a rotary encoder 166 as well as drive nut sensors 164a, 164b and 164c. In some embodiments, the drive nut sensors are aligned in an axis along the length of the lead screw 124 such that there is a proximal sensor 164a, a middle sensor 164b and a distal sensor 164c. In certain embodiments the sensors of the plunger drive mechanism 118 are in communication with the control system 150 before, during and after the injection program. In some embodiments, the sensors of the plunger drive mechanism 118 communicate information to the control system 150 prior to the injection related to the spatial location of the plunger drive unit 132 related to the starting position for the purpose of determining the extensional length of the plunger rod 228. In some embodiments, the sensors of the plunger drive mechanism 118 communicate information to the control system 150 during the injection for the purpose of recording the duration of the injection. In certain embodiments, the control system 150 includes a motion control program, for example a PID controller algorithm, that receives input from the rotary encoder 166 as well as the drive nut sensors 164a, 164b, 164c.

In various embodiments, the operating program stored in the memory of the control system 150 contains instructions for at least (a) moving the cartridge module carrier 110 from an extended position (FIGS. 4A and 4B) to a retracted position (FIG. 4C), resulting in the removal of the needle shield 234 after the pre-filled cartridge 220 has been loaded, (b) moving the hypodermic needle 226 from a retracted position (FIG. 4C) to an extended position (FIGS. 4A and 4B beyond the distal end 108 of the injector 100 (e.g., through a needle aperture 142), (c) providing force to the plunger head 230 in order to expel the medicament 222 from the pre-filled cartridge 220 through the needle 226 in a controlled manner, and (d) moving the hypodermic needle 226 from an extended position (FIG. 4B) to a retracted position (FIG. 4C) following completion of the injection. In some embodiments, the operating program is standard for all medicaments 222 delivered by the injector 100. In various embodiments, there is a specific operating program for each medicament 222 delivered by the injector 100. In certain embodiments, the (b) needle extension step of the operating program can be unique to the optimal injection depth of each medicament 222 delivered by the injector 100. In certain embodiments, the operating program can store multiple injection depths for each medicament 222. In certain embodiments, the (a) needle-shield 234 removal can be initiated by the user interface 152 and (b) needle insertion, (c) injection of medicament 222, and (d) needle retraction can be initiated by engagement of an activation switch 180 on the injector 100. In certain embodiments, the (c) force provided to the plunger head 230 in order to deliver a medicament 222 is specific to each medicament. In one arrangement, the cartridge drive mechanism 134, which facilitates the movement of the cartridge module carrier 110 and connected cartridge module 200 for the retraction and extension steps of the operating program, includes an electromechanical actuation system (e.g. motor with a rack and pinion). In another embodiment the cartridge drive mechanism 134 includes a purely mechanical actuation system (e.g. a spring). In further embodiments, the cartridge drive mechanism 134 includes a spring and an electromechanical actuation system. In various embodiments, the cartridge drive mechanism 134 is capable of highly controlled axial movement, including (b) needle insertion at various depths and subsequent (d) needle retraction.

In various embodiments, the plunger drive mechanism 118 comprises an electromechanical actuation system, including a motor 120 (e.g., a servo motor) configured for a second actuation event of driving the plunger rod 228 through the barrel 224 of a pre-filled cartridge 220 at a controlled rate and over a pre-determined distance for expelling the medicament 222 into the subject. In various embodiments, the motor 120 may be connected to an actuator 122 comprising a lead screw 124 and a lead nut 126 connected to a plunger drive unit 132. The actuator 122 can translate the rotational motion of an output shaft 128 into linear motion plunger drive unit 132. In certain embodiments, the motor is directly linked to the linear actuator. In other embodiments, a set of gears 130 may be positioned between the output shaft 128 and the actuator 122 for reducing the speed of the motor 120 and/or increasing the torque output. In various embodiments, the gear set 130 can be optimized for delivery of medicaments 222 having varying viscosity.

In some embodiments, the control system 150 includes memory for storing data related to doses received, injections performed, user-generated injection parameter, etc. For example, the memory can store programs specific for a container's dimensions and a medicament's rheology. The control system 150 can use input from sensors, such as the thermal sensor 160, in combination with the stored rheology programs in order to calculate a medicament's viscosity. The memory also stores programs for operating the injector 100, such as injection force calculation and corresponding motor speed. The control system's processor can be a master control unit for calculating and performing parameters of a desired injection.

Figure 6:
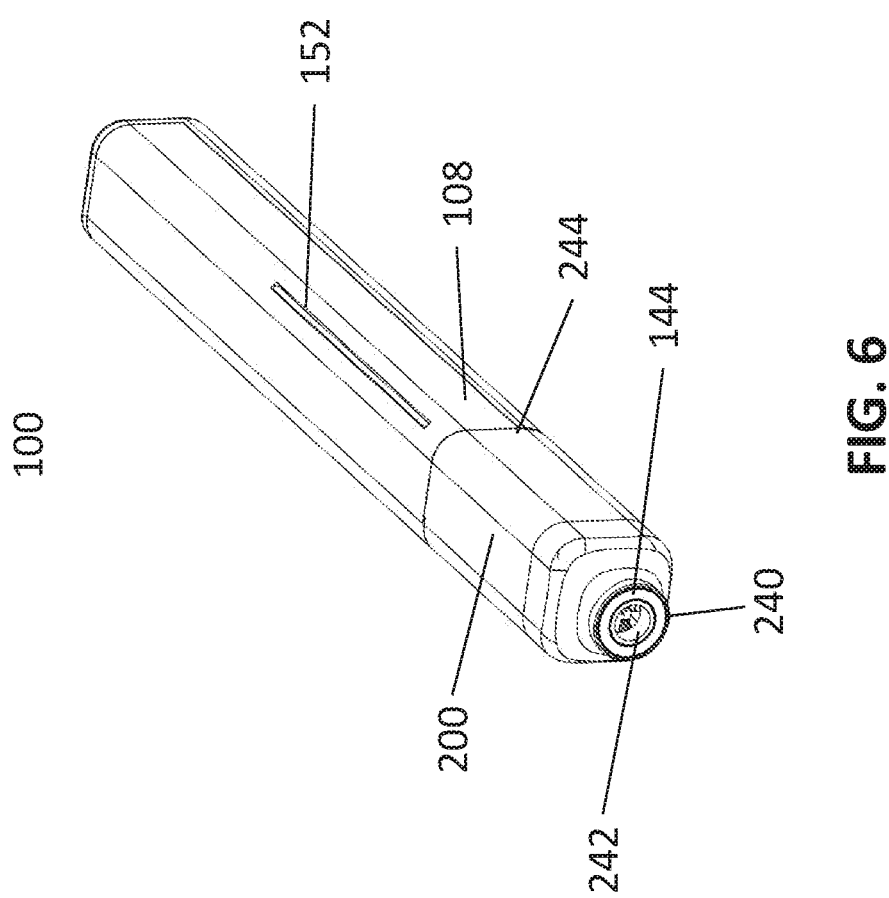
FIG. 6 is a front-side view of the injector assembly, comprising an injector and a cartridge module as two separate assemblies that are connected to form the functional automatic injector system, in accordance with another embodiment of the present technology.

FIG. 6 is a front-side view of an injector 100 with a cartridge module 200 attached to it, in accordance with an embodiment of the present technology. In some embodiments, the cartridge module 200 is a subassembly separate from the injector subassembly 100. The advantage of a cartridge module subassembly 200 is a greater degree of dimensional freedom, allowing the injector assembly 10 to accept larger and wider pre-filled cartridges 220 without enlarging the injector subassembly 100, which needs to be comfortably held in the hand of a user. In some embodiments, the cartridge module subassembly 200 can be operatively connected to the injector subassembly 100 by removably attaching the proximal end 244 of the cartridge module 200 with the distal end 108 of the injector 100. In certain embodiments, a cartridge module 200 can be removably attached by screwing on the proximal end 244 onto the distal end 108 of the injector 100. In other embodiments, the cartridge module 200 can be removably attached with a latching mechanism by pressing the proximal end 244 onto the distal end 108 of the injector 100. In some embodiments, a needle aperture 242 is located on the distal end 240 of the cartridge module 200 subassembly through which a hypodermic needle 226 can extend. In some embodiments, the distal end 240 of the cartridge module 200 contains a patient sensor 144.

Figure 7:
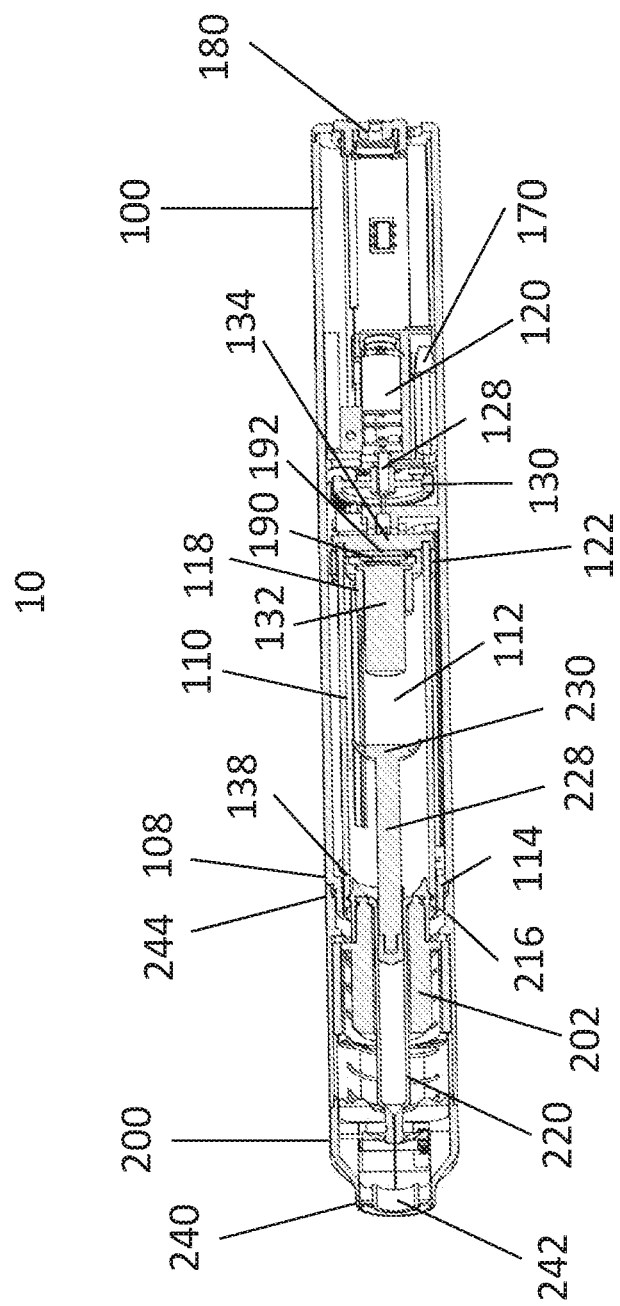
FIG. 7 is a cross-sectional side view of the apparatuses comprising an automatic injection system, including a pre-filled cartridge, the cartridge module shown in FIG. 6, and the injector shown in FIG. 6, in accordance with an embodiment of the present technology.

FIG. 7 is a cross-sectional side view illustrating the components of the injector assembly 10 shown in FIG. 6, including a cartridge module subassembly 200 loaded with a pre-filled cartridge 220 and operatively connected to the injector subassembly 100. In some embodiments, a cartridge module 200 is operatively connected to the injector 100 only when the standard fittings 216 of the cartridge module 200 are properly connected to the engagement features 114 of the injector 100. In some embodiments, the standard fittings 216 are located on the proximal end 244 of the cartridge module 200, and the engagement features 114 are located on the distal end of the injector 100. In some embodiments, the standard fittings 216 are located on the plunger drive unit aperture 246 of the cartridge module 200, and the engagement features 114 are located on the distal end 138 of the cartridge module carrier 110.

In some embodiments, an operative connection between the cartridge module subassembly 200 and the injector subassembly 100 centrally aligns the internal cavity 202 of a cartridge module 200 with the axis of the plunger drive unit 132. An operative connection results in the cartridge module identification element 214 successfully communicating information to the identification reader 116. In some embodiments, the identification element 214 is located on the proximal end 244 of the cartridge module 200, and the identification reader is located on the distal end 108 of the injector 100. In other embodiments, the identification element 214 is located on the proximal end of the internal cavity 202, and the identification reader 216 is located on the distal end 138 of the cartridge module carrier 110. In further embodiments, the injector 100 will only operate when a signal is received from the identification reader 116 communicating with the identification element 214. In certain embodiments, there are peripheral electronic components in the cartridge module 200, such as a thermal sensor 160. An operative connection between the cartridge module subassembly 200 and the injector subassembly 100 is required to complete the electrical connection between the two subassemblies, communicating power and information between the control system 150 and peripheral electronics.

In referring to FIG. 7, certain embodiments include a single motor 120 for driving both the plunger drive mechanism 118 and the cartridge drive mechanism 134. The motor 120 is coupled to a gear set 130 by an output shaft 128. In some embodiments, the gear set 130 is coupled to a lead screw 124, which translates rotational motion of the motor 120 into linear motion of the actuator 122. In some embodiments, the actuator 122 is physically connected to the plunger drive mechanism 118. In some embodiments, the proximal end of the plunger drive mechanism 118 contains a magnet 190 which pairs with a magnet 192 on the cartridge drive mechanism 134. As the actuator 122 moves distally, the cartridge drive 134 remains coupled to the plunger drive mechanism 118 and moves distally as well. In certain embodiments, the carrier distal end 138 is rigidly attached to the internal cavity 202. As the actuator 122 moves distally, the internal cavity 202 also moves distally, extending the needle 226 through the needle aperture 242. As the internal cavity 202 reaches its distal-most position within the cartridge module subassembly 200, the actuator 122 overcomes the attractive force between the plunger drive magnet 190 and the cartridge drive magnet 192, leaving the cartridge drive 134 stationary in its distal-most position within the injector subassembly 100.

In certain embodiments, the actuator 122 continues to move forward until the plunger drive unit 132 engages the plunger head 230. In certain embodiments, the plunger drive unit 132 incorporates a force sensor connected to the control system 150, indicating when the plunger drive unit 132 has engaged the plunger head 230. In other embodiments, the control system 150 identifies contact between the plunger drive unit 132 and the plunger head 230 based on an increase in load on the motor 120. Once the plunger drive unit 132 engages the plunger head 230, the actuator 122 moves distally at a predetermined rate, driving the plunger rod 228 into the barrel 224 and expelling the medicament 222 through the needle 226. The actuator 122 continues to move distally over a predetermined linear distance according to the required dose of medicament 222 stored in the control system 150. Once the actuator 122 reaches its predetermined distal endpoint within the injector subassembly 100, the actuator 122 then retracts proximally to the point where the plunger drive magnet 190 reengages the cartridge drive magnet 192. In certain embodiments, as the actuator 122 continues to move to its proximal-most position, the cartridge drive mechanism 134 moves proximally with the internal cavity 202, retracting the needle 226 back into the needle housing 204. In some embodiments, an additional element, for example a spring, configured to increase delivery force of the drive mechanism is integrated into the injector assembly. The spring can be incorporated around a portion of the lead screw 124. The compression of the spring can be controlled by the movement of the lead screw 124 driven by the motor 120. As the motor 120 moves the lead screw 124, force is delivered to the plunger drive unit 132 by both the spring and the actuator 122. The spring can be weaker than the maximum force delivered by the motor 120, so that upon completion of medicament delivery to a patient, the motor 120 can compress the spring during movement of the lead screw 124 back to the starting position.

Selected Examples of Custom Modules and Associated Cartridges

Figure 8A:
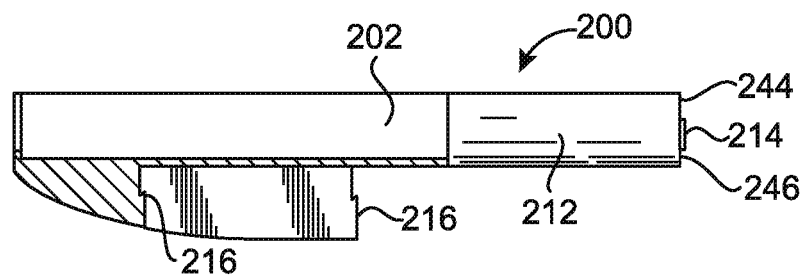
FIGS. 8A and 8B are a cross-sectional side view and front view, respectively, of the cartridge module shown in FIG. 1C, illustrating the standard features shared across different cartridge modules in accordance with an embodiment of the present technology.
Figure 8B:
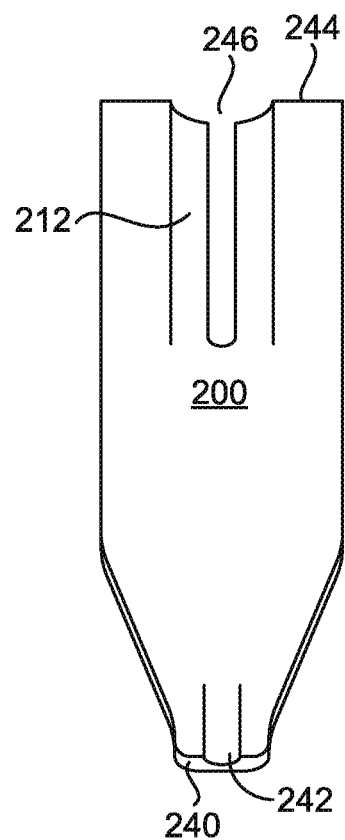

FIGS. 8A and 8B are a cross-sectional side view and a front view, respectively, of the cartridge module 200 shown in FIGS. 1A-5, illustrating the standard features shared among distinct types of cartridge modules 200 of the present technology. In some embodiments, an operative connection between a cartridge module 200 and the injector 100 is formed only when a cartridge module 200 is properly installed within the cartridge module carrier 110 of an injector 100. In certain embodiments, proper installation of a cartridge module 200 within the cartridge module carrier 110 aligns the distal end 240 of the cartridge module 200 with the distal end 108 of the injector 100. In some embodiments, the internal cavity 202 of a cartridge module is centrally aligned with the axis of the cartridge module needle aperture 242 and the needle aperture 142 of an injector 100. In certain embodiments, a cartridge module 200 contains an identification element 214 oriented for communication with the cartridge module identification code reader 116. In various embodiments, the identification element 214 contains a unique identification code specific to the cartridge module 200. In further embodiments, the identification code contained within the identification element 214 is read by a cartridge module identification code reader 116 and interpreted by the control system 150.

In various embodiments, a cartridge module 200 contains standard fittings 216 that are shared among distinct types of cartridge modules 200. In certain embodiments, the standard fittings 216 are shaped to securely connect to engagement features 114 located on the cartridge module carrier 110 of the injector 100. In further embodiments, the standard fittings 216 are precisely located on the cartridge module 200 in a way that dictates proper orientation of the cartridge module when connected to the engagement features 114 of the cartridge module carrier 110. In certain embodiments, the standard fittings 216 must be properly connected to the engagement features 114 in order for cartridge module identification code reader 116 to successfully read the information contained in the cartridge module identification element 214. In further embodiments, the injector 100 will only operate when a signal is received from the cartridge module code reader 116 communicating with the identification element 214.

In certain embodiments, a standard plunger housing 212 forms the proximal end of the cavity 202 of distinct types of cartridge modules 200. In some embodiments, the plunger housing 212 is connected to the plunger drive unit aperture 246 on the proximal end 244 of the cartridge module 200. In some embodiments, the cavity 202 is centrally aligned with the plunger drive unit 132 of the plunger drive mechanism 118, allowing for the plunger drive 132 unit to enter the cavity 202 through the plunger drive unit aperture 246 and move longitudinally through the plunger housing 212 towards the distal end of the cartridge module 200. In further embodiments, there is an opening that runs longitudinally along the bottom of the plunger housing 212 that allows the lead screw 124 of the actuator 122 to be located below the plunger drive unit 132. In such embodiments, the lead nut 126 is connected to the plunger drive unit 132 through the opening on the bottom of the plunger housing 212. In various embodiments, the standard features described above enable distinct types of cartridge modules 200 to facilitate the full functionality of the injector 100, including the instructions contained in the operating program stored on the control system 150, such as needle insertion, medicament injection, and needle retraction.

Figure 9A:
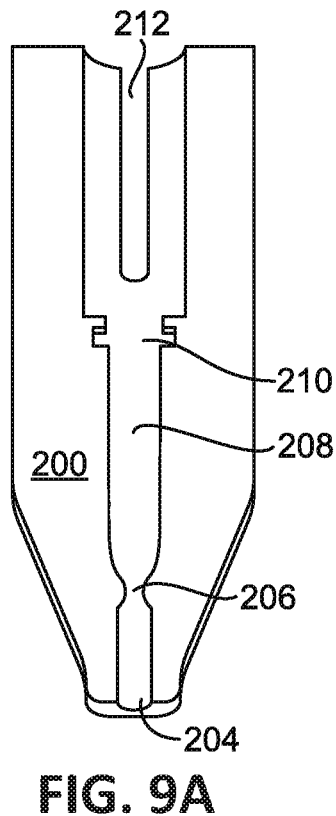
FIGS. 9A, 9B and 9C are a front view of three distinct cartridge modules, illustrating the standard and custom features of the cartridge module in accordance with an embodiment of the present technology.
Figure 9B:
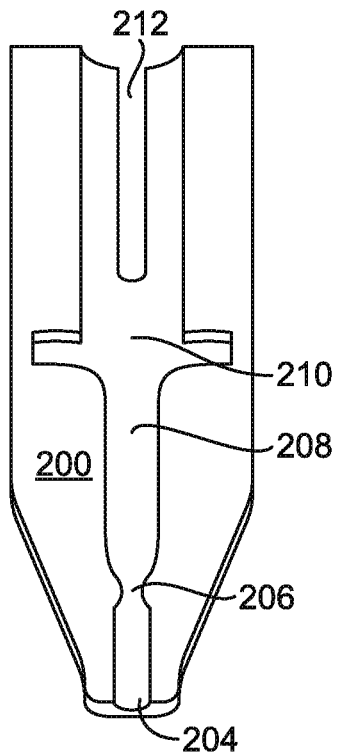
Figure 9C:
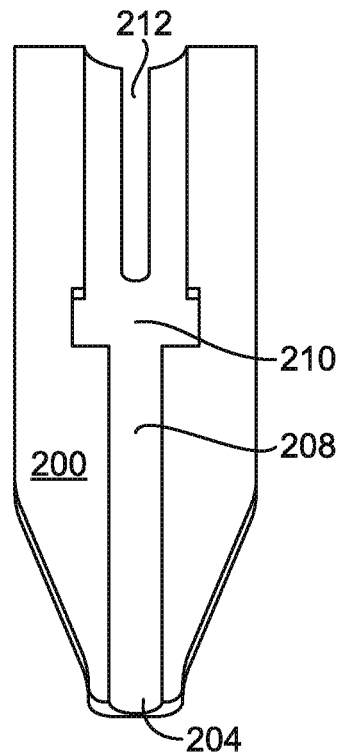

FIGS. 9A, 9B and 9C are a front view of three distinct types of cartridge modules 200 according to the embodiments shown in FIGS. 1A-5. In certain embodiments, a cartridge module cavity 202 is composed of distinct sections designed to accept various portions of a pre-filled cartridge 220 when loaded into the cartridge module 200 in the proper orientation. In some embodiments, a cartridge module cavity 202 includes a needle housing 204, a barrel housing 208 and a plunger housing 212. In various embodiments, the plunger housing 212 is the only portion of the cavity 202 that is standard among distinct types of cartridge modules 200. In certain embodiments, the needle housing 204 and the barrel housing 208 are dimensionally specific for the needle 226 and barrel 224, respectively, of a particular type of pre-filled cartridge. In some embodiments, the needle housing 204 comprises the distal portion of the cavity 202 and is connected to the needle aperture 242 of the cartridge module 200. The cartridge module cavity 202 can also include features, such as shoulder supports 206 and flange supports 210, designed to hold in place a pre-filled cartridge 220 during the normal operations of the injector 100. In certain embodiments, the shoulder supports 206 and flange supports 210 are dimensionally restrictive to the barrel 224 and the flange 232 a particular type of pre-filled cartridge 220. In some embodiments, the shoulder supports 206 can be specific to both the dimensions and materials of a barrel 224. For example, the shoulder supports 206 for a plastic 1 mL standard syringe can be different from the shoulder supports 206 for a glass 1 mL standard syringe. The shoulder supports 206 can be responsible for accepting and alleviating the force transferred from the plunger drive mechanism 118 through the pre-filled cartridge 220, and can be designed to prevent breakage of the barrel 224 under such stress. In certain embodiments, the portions of the cavity 202, including the needle housing 204 and the barrel housing 208, as well as the support features of the cavity 202, including the shoulder supports 206 and the flange supports 210, can be designed to enable the full functionality of the loaded pre-filled cartridge 220. For example, a particular type of cartridge module 200 may have a cavity 202 that is capable of securely holding a pre-filled cartridge 220 in place during the operations of the injector 100, but also allow for the deployment of an automatic needle-shielding feature by the pre-filled cartridge after the completion of the injection.

Figure 10A:
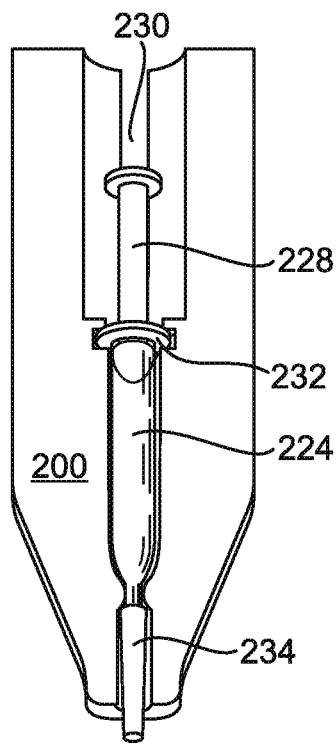
FIGS. 10A, 10B and 10C are a front view of the three distinct cartridge modules shown in FIGS. 9A, 9B and 9C, respectively, illustrating how the standard and custom features of the cartridge module removably secure diverse pre-filled cartridges in accordance with an embodiment of the present technology.
Figure 10B:
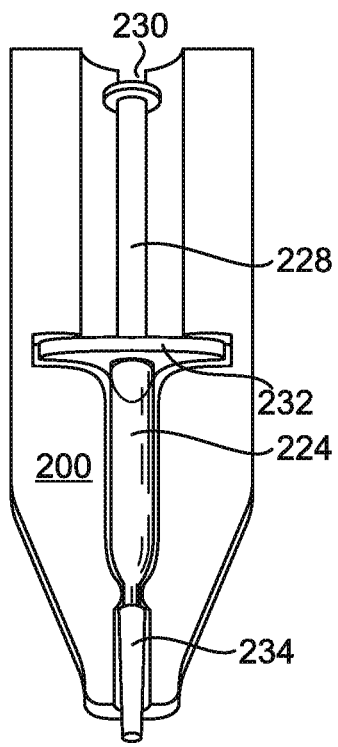
Figure 10C:
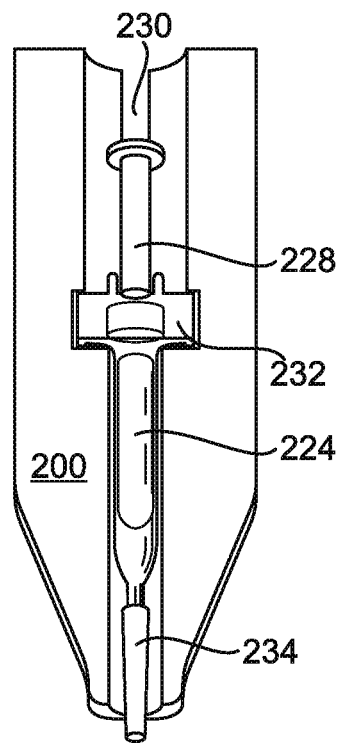

FIGS. 10A, 10B and 10C are a front view of three distinct types of cartridge modules 200 shown in FIGS. 9A, 9B, and 9C, respectively, each housing the pre-filled cartridge 220 that it was specifically designed to accept. In various embodiments, the type of pre-filled cartridge 220 that a particular cartridge module 200 can accept is determined by the dimensions of the cavity 202, including the needle housing 204, the should supports 205, the barrel housing 208, and the flange support 210, but not the plunger housing 212, which is dimensionally generic and shared among distinct types of cartridge modules 200.

In certain embodiments, a particular type of cartridge module 200 can include an upper portion installed on the inner surface of the door 102. In some embodiments, the top portion of the cartridge module 200 can include a component involved in the automated removal of the needle shield prior to injection 234. In some embodiments, the top portion of the cartridge module 200 can include support features that hold the pre-filled cartridge in place, in addition to- or in replace of the shoulder supports 206 and the flange supports 210 of the cavity 202. In some embodiments, the top portion of the cartridge module 200 can include an adaptor for the thermal transducer element 162 of the injector 100 designed to physically couple the thermal transducer 162 to the barrel 224 of a loaded pre-filled cartridge 220.

FIGS. 11A, 11B and 11C are a front view of three distinct types of cartridge module subassembly 200 according to the embodiments shown in FIGS. 6 and 7. When the appropriate pre-filled cartridge 200 is loaded properly into the cartridge module subassembly 200, the hypodermic needle 226 is located within the needle housing 204 on the proximal end 244 of the cartridge module 200. In some embodiments, the different types of cartridge modules 200 have distinct sizes and shapes, based on the dimensions of the pre-filled cartridge 220 that it is designed to accept. In other embodiments, every type of cartridge module subassembly 200 has the same size and shape. The dimensions of the inner cavity 202 are designed to the dimensional requirements for a specific type of pre-filled cartridge 220, including the needle housing 204, the shoulder support 206, the barrel housing 208 and the flange support 210. In some embodiments, the cartridge module subassembly 200 includes a plunger housing 212 on the distal end 240. In other embodiments, the plunger rod 228 and plunger head 230 extend out of the cartridge module subassembly 200 through the plunger drive unit aperture 246 on the distal end 240.

FIGS. 12A, 12B and 12C are a front cross-sectional view of three distinct types of cartridge module subassemblies 200 shown in FIGS. 11A, 11B and 11C, respectively, each housing the pre-filled cartridge 220 that it was specifically designed to accept. In some embodiments, the internal cavity 202 housing the pre-filled cartridge 200 can move a pre-determined linear distance axially within the cartridge module subassembly 200. In some embodiments, movement of the internal cavity 202 is controlled by the cartridge module carrier 110. In some embodiments, there is a spring 236 connected to the internal cavity 202 housing the pre-filled cartridge 220. In certain embodiments, the spring 236 is responsible for holding the pre-filled cartridge 220 in a position in which the needle 226 is retracted within the needle housing 204. In such embodiments, the cartridge drive mechanism 134 can move the internal cavity 202 distally within the cartridge module 200, compressing the spring 236 and extending the needle 226 through the needle aperture 242. In such embodiments, the cartridge drive mechanism 134 can also move the internal cavity 202 proximally within the cartridge module 200, releasing the spring 236 and retracting the needle 226 back into the needle housing 204. In certain embodiments, the spring 236 moves the internal cavity 202 distally within the cartridge module 200, extending the needle 226 through the needle aperture 242. In such embodiments, the cartridge drive mechanism 134 moves the internal cavity 202 proximally within the cartridge module 200, compressing the spring 236 and retracting the needle 226 back into the needle housing 204. In some embodiments, the cartridge module carrier 134 is responsible for releasing the compressed spring 236. In some embodiments, magnets are responsible for holding the spring 236 in a compressed state.

In various embodiments, cartridge modules 200 differ beyond their physical dimensions and the pre-filled cartridge they are designed for. In some embodiments, distinct cartridge modules 200 are designed for the same pre-filled cartridge 220, but contain different components. For example, a premium version of a specific type of cartridge module 200 may contain a heating element to quickly warm the loaded pre-filled cartridge 220 to room temperature, while a basic version of the same type of cartridge module 200 does not have the same heating component. In further embodiments, one cartridge module 200 designed for a single type of pre-filled cartridge 220 can facilitate different functions based on the identification element 214. For example, the injector 100 may record the temperature for one type of medicament 222 that needs to be refrigerated, while ignoring the temperature for another medicament when a physically identical cartridge module 200 with a different identification element 214 is operatively connected. In such embodiments, the information necessary for the injector 100 to perform the appropriate functions for the operatively connected cartridge module 200 is contained in the identification element 214 and programmed into the control system 150.

In referring to FIGS. 6, 7 and 11A-12C together, the injector assembly 10 comprises two separate subassemblies, including a cartridge module 200 and an injector 100. The injector subassembly 100 must be operatively connected to a cartridge module subassembly 200 in order to automatically deliver a dose of medicament to a subject. In some embodiments, the cartridge module 200 is a disposable subassembly allowing for single use with the reusable injector 100. In such embodiments, the disposable cartridge module 200 can be loaded with a pre-filled cartridge 220 at the point of production. In such embodiments, the disposable cartridge module 200 is discarded along with the pre-filled cartridge 220 after the injection. In other embodiments, the cartridge module 200 is a reusable subassembly. In such embodiments, the cartridge module 200 must be disconnected from the injector 100 in order to load a pre-filled cartridge 220 into it. In such embodiments, the reusable cartridge module 200 is loaded with a pre-filled cartridge 220 at the point of care. In such embodiments, the pre-filled cartridge 220 is removed from the internal cavity 202 and discarded after each injection, but the cartridge module 200 is kept and reused for each subsequent injection.

In some embodiments, the plunger rod 228 and plunger head 230 extend out beyond the proximal end 244 of the cartridge module subassembly, through the plunger drive unit aperture 246. In such embodiments, the plunger housing 212 is located within the injector subassembly 100. In some embodiments, the cartridge module carrier 110 forms the plunger housing 212. In further embodiments, there is an opening that runs longitudinally along the bottom of the cartridge module carrier 110 that allows the lead screw 124 of the actuator 122 to be located below the plunger drive unit 132. In such embodiments, the lead nut 126 is connected to the plunger drive unit 132 through the opening on the bottom of the cartridge module carrier 212. In various embodiments, the standard features described above enable distinct types of cartridge module subassembly 200 to facilitate the full functionality of the injector subassembly 100, including the instructions contained in the operating program stored on the control system 150, such as needle insertion, medicament injection, and needle retraction.

In some embodiments, the present disclosure provides an injector assembly for automatically delivering a dose of a medicament to a subject, the injector assembly comprising an activation switch for initiating automatic delivery of the dose of the medicament; a needle aperture at a proximal end of the injector assembly and for enabling an injection needle to pass therethrough; a standard connection means for operatively connecting a removable cartridge module to the reusable injector, the removable cartridge module including (a) a needle housing for dictating the range or possible injection depths, (b) a plunger housing for aligning a plunger assembly with the plunger drive unit, (c) an identification code associated with the pre-filled cartridge and medicament contained within, and (d) a cavity for reversibly securing a pre-filled cartridge, the pre-filled cartridge including: (i) a barrel for containing the medicament and having a proximal end and a distal end, (ii) a needle operably connected to the proximal end of the barrel, (iii) a plunger assembly including a plunger rod having a proximal end initially located near the distal end of the barrel, and a distal end including a plunger head, and (iv) an amount of the medicament; a plunger drive mechanism for applying pressure to the plunger assembly, the plunger drive mechanism including a motor operably connected to the activation switch, and an actuator operably connected to the motor and the plunger assembly; at least one engagement feature for securing the removable cartridge module to the injector; a cartridge drive assembly for moving the pre-filled cartridge towards the distal end of the injector assembly, the cartridge drive assembly including at least one gear element operably connected to the motor and the activation switch; a code reader for reading the identification code associated with the medicament and pre-filled cartridge; a sensor for detecting contact with skin of the subject; and a battery operably connected to the motor.

In some embodiments, the cartridge module includes a separate top portion integrated with the door.

In some embodiments, the activation switch is at a proximal end.

In some embodiments, the needle aperture is at a distal end.

In some embodiments, the injector assembly is configured to prevent activation of the cartridge drive assembly and/or the plunger drive assembly if the sensor does not detect skin of the subject when the activation switch is pressed.

In some embodiments, the injector assembly is configured to stop activation of the cartridge drive assembly and/or the plunger drive assembly if the sensor stops detecting skin of the subject after the activation switch is pressed.

In some embodiments, the door includes at least one latch.

In some embodiments, the door is rotatably attached to the body of injector assembly by at least one hinge.

In some embodiments, the patient sensor is a pressure sensor.

In some embodiments, the patient sensor detects skin using electrical conductivity.

In some embodiments, the removable cartridge module further includes a feature conforming to a flange of the pre-filled cartridge.

In some embodiments, upon activation of the activation switch and detection of patient contact by the sensor, the cartridge module carrier drive assembly moves the cartridge module a first pre-determined distance towards the distal end of the injector assembly and optionally thereafter moves the cartridge module away from the distal end of the injector assembly by at least the first pre-determined distance. In some embodiments, the first pre-determined distance is associated with the identification code.

In some embodiments, upon activation of the activation switch and detection of skin by the sensor, the plunger drive mechanism moves the plunger a second pre-determined distance towards the distal end of the injector assembly. In some embodiments, the second pre-determined distance is associated with the identification code.

In some embodiments, the barrel includes the medicament in an amount of at least about 1 dose. In other embodiments, the barrel includes the medicament in an amount of at least 2 doses, at least 3 doses, at least 4 doses, at least 5 doses, at least 6 doses, at least 7 doses, at least 8 doses, at least 9 doses, at least 10 doses, at least 11 doses, at least 12 doses, at least 13 doses, at least 14 doses, at least 15 doses, at least 16 doses, at least 17 doses, at least 18 doses, at least 19 doses, at least 20 doses, or more than 20 doses.

In some embodiments, the injector assembly further comprises a control system including a microcontroller configured to store a plurality of identification codes, and store first and/or second pre-determined distances associated with each identification code. In some embodiments, the control system stores a library of injection programs, each one associated with an identification code. In some embodiments, the injection program contains instructions for performing all steps involved in the operations of the device. In some embodiments, the control system further includes a transceiver for receiving data associated with identification codes from a server and/or for sending data associated with identification s to a server.

In some embodiments, the microcontroller is further configured to cause the plunger drive mechanism to move the plunger the second pre-determined distance by exerting an injection force on the plunger based on one or more of: a pressure between the injection assembly and the subject as determined by the pressure sensor, the rotary encoder, a temperature of the medicament, and the identification code.

In some embodiments, the present disclosure provides a cartridge module comprising a needle housing for dictating the range of injection depths possible; a plunger housing for aligning a plunger assembly with the plunger drive unit; a cavity for reversibly securing a cartridge pre-filled with a medicament; an identification code associated with the medicament; at least one fitting for removably engaging the cartridge module in an injector assembly; and at least one fitting for engaging the cartridge module with a cartridge drive assembly, optionally wherein the cartridge drive assembly is integrated with the injector assembly.

In some embodiments, the cartridge module further includes a housing that is open on at least one face and configured to mate with a door of an injection assembly.

In some embodiments, the cartridge module further comprises a shoulder support for mating with a pre-filled cartridge. In some embodiments, the cartridge module further comprises a flange support for mating with a pre-filled cartridge. In some embodiments, the shoulder support and/or the flange support are configured to prevent mating with an undesired pre-filled cartridge.

In some embodiments, the cavity includes a barrel housing between shoulder support and flange support, optionally configured to prevent mating with an undesired pre-filled cartridge.

In some embodiments, the needle housing is configured to prevent mating with an undesired pre-filled cartridge.

In some embodiments, the needle housing is configured to align or mate with a needle aperture of an injector device.

In some embodiments, the needle housing shields a needle of a pre-filled cartridge such that administration of the medicament through a needle of the pre-filled cartridge is prevented until the cartridge module is operatively connected to an injector assembly.

Selected Embodiments of Methods Associated with Injection Assemblies and Apparatuses Several suitable methods are disclosed herein and discussed further below; however, one of ordinary skill in the art will recognize a plurality of methods suitable to produce and operate injection assemblies and to deliver a dose of medicament in a controlled manner. With respect to the two embodiments illustrated in FIGS. 1A-12C, the injector can be used in combination with a cartridge module for automated delivery of a medicament to a subject. Further methods include tools for producing a wide variety of cartridge modules that are all dimensionally and functionally compatible with the injector for the automated delivery of a medicament. Additional methods include steps for automatically determining the identity of a medicament loaded into the injection assembly before or after the delivery of the medicament.

Figure 13A:
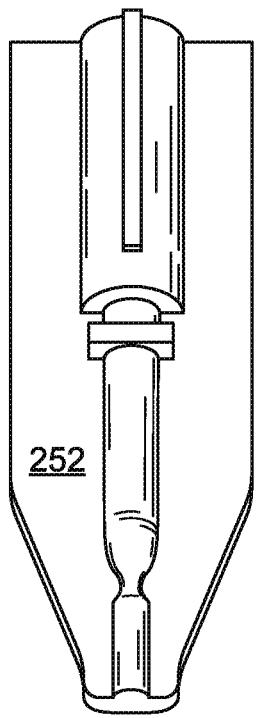
FIGS. 13A, 13B, 13C and 13D are a front view of three distinct custom molds and a standard mold, respectively, for producing the cartridge modules shown in FIGS. 9A, 9B and 9C, respectively, the standard mold together with a custom mold comprise a method for producing a wide variety of unique cartridge modules in accordance with an embodiment of the present technology.
Figure 13B:
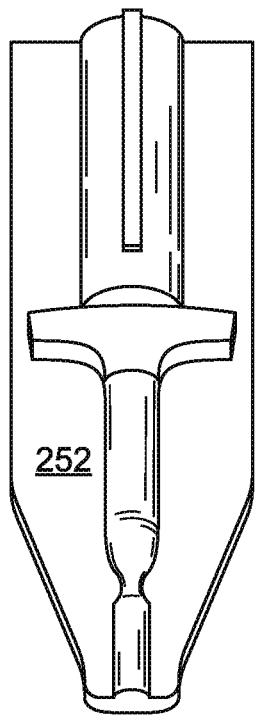
Figure 13C:
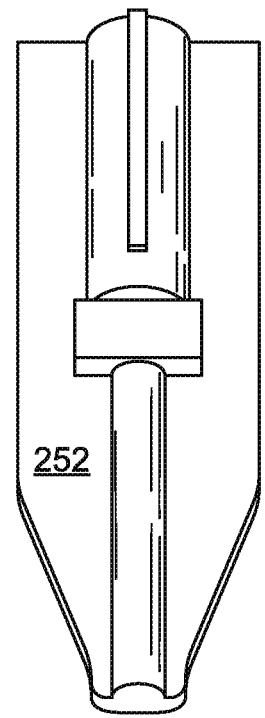
Figure 13D:
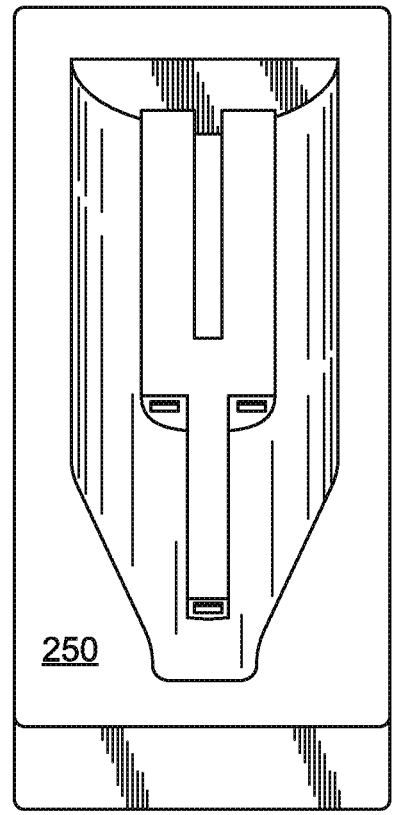

FIGS. 13A, 13B and 13C are a front view of three distinct custom molds, and FIG. 13D is a front view of the standard mold, a custom mold and standard mold together can be used for the production of a cartridge module. The custom molds 252 are dimensionally specific for a particular type of pre-filled cartridge, and are responsible for forming the internal cavity of the cartridge module where the pre-filled cartridge will be housed. In certain embodiments, the custom molds are dimensionally generic over the portion that is responsible for forming the plunger housing of the internal cavity. In certain embodiments, the custom molds are dimensionally specific over the portions that form the needle housing, the barrel housing, the shoulder support features and the flange support features. The standard mold 250 is dimensionally generic for each pre-filled cartridge, and is responsible for forming the base of the cartridge module that connects to the cartridge module carrier of the injector in a way that facilitates the operations of the injector. In certain embodiments, the standard mold contains features that form the standard fittings of a cartridge module, which facilitate the secure connection with the engagement features of the cartridge module carrier. In certain embodiments, the standard mold contains features that form the standard plunger housing of a cartridge module. In some embodiments, a two-piece cartridge module includes an upper portion that is installed on the inner surface of the door of the injector. In such embodiments, there is a custom mold and a standard mold for the upper portion, the custom mold forming the features that face the lower portion of the cartridge module, while the standard mold forms the generic features that connect to the door.

A method for producing a variety of cartridge modules includes the combination of the standard mold (FIG. 13D) with one of a plurality of custom molds (FIGS. 13A, 13B and 13C) in a manufacturing process, such as injection molding. In certain embodiments, the standard mold form the base of the injection molding tool, and the custom mold forms the top. In certain embodiments, there is a standard mold for the lower portion of a cartridge module, as well as a standard mold for the upper portion. In such embodiments, there are also custom molds for a variety of two-piece cartridge modules, each type includes a lower custom mold and an upper custom mold that is combined with the lower and upper standard mold, respectively, in a manufacturing process. In certain embodiments, the standard mold and a particular custom mold are made of the same material. In certain embodiments, the standard mold and a particular custom mold are made from different types of material. In one embodiment, the standard mold is made of a material suitable for high volume manufacturing, and a particular custom mold is made of a material suitable for low or mid-volume manufacturing.

Figure 14:
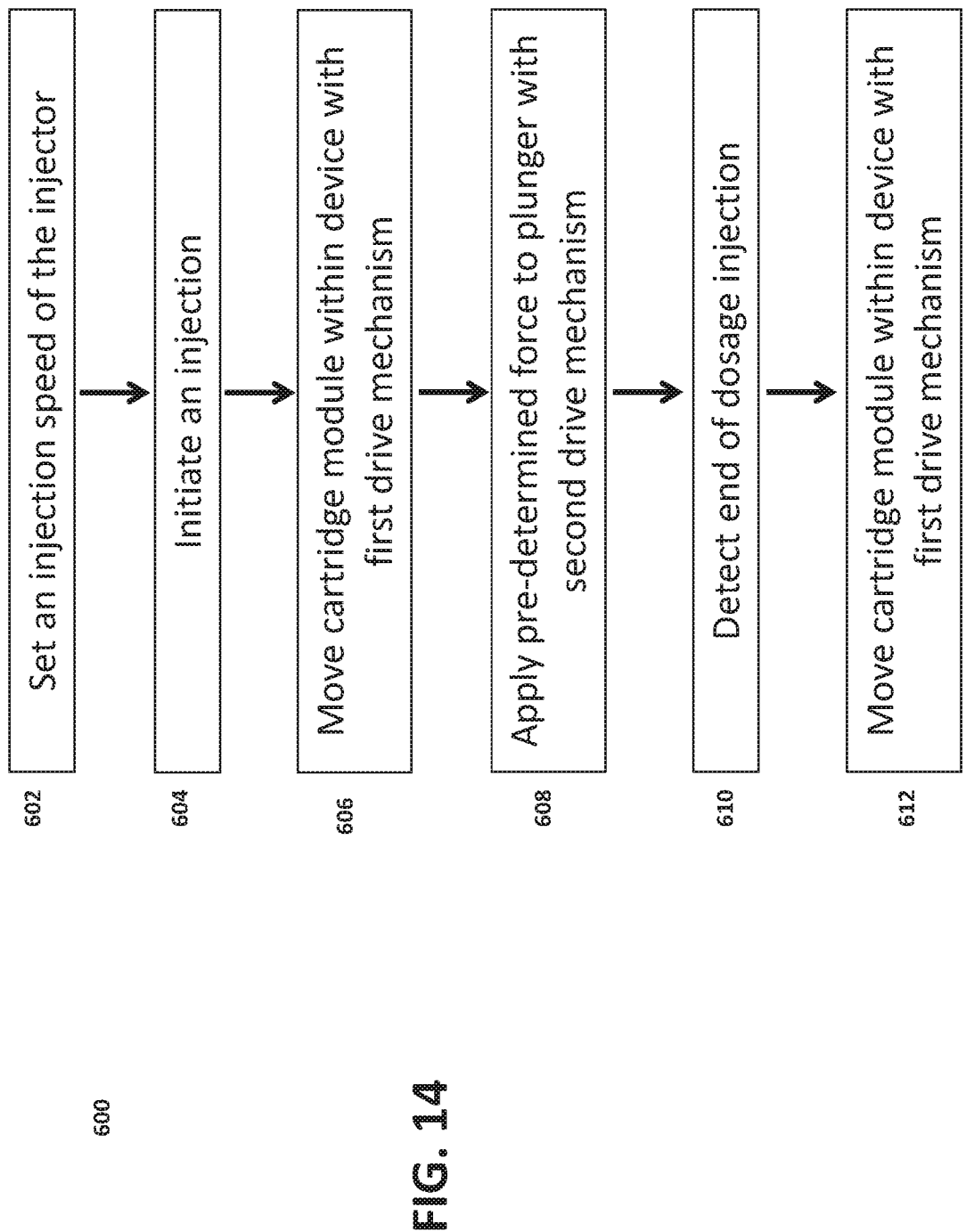
FIG. 14 is a flow diagram illustrating a method for automated delivery of a dose of a medicament in accordance with another embodiment of the present technology.

FIG. 14 is a flow diagram illustrating a method 600 for automated delivery of a medicament in accordance with an embodiment of the present technology. The method 600 can begin with a user removing a pre-filled cartridge containing a dose of the medicament out of refrigerated storage (if necessary) in order to raise a temperature of the medicament to room temperature, for example. An injector may be loaded with a dose of the medicament by opening the door of the injector and placing the pre-filled cartridge into the cavity of the cartridge module, and closing the door. The method 600 continues with setting an injection speed of the injector (block 602). In some embodiments, and prior to injection of the dosage, the user may select a desired injection speed via the user interface on the injector or wirelessly through a software application. In another embodiment, the injection speed can be a speed selected based on the characteristics of the medicament and/or a manufactures's preference. In one embodiment, the selection of an injection speed initiates the retraction of the needle into the injector, resulting in the automatic removal of the needle shield. In another embodiment, needle-shield removal is initiated by a separate switch/step.

Prior to initiating an injection, the lower surface of the injector, including the patient sensors (e.g. skin sensor and pressure sensor) on the distal tip of the injector can be positioned at an injection site with the device held at an approximate 90° angle relative to the injection surface. In other embodiments, the lower surface of the injector can be positioned at other angles relative to the injection surface (e.g., between about 80°-90°, between about 70°-90°, between about 60°-90°, etc.). The method 600 also includes initiating an injection of the medicament when an injection switch is engaged (block 604). The switch may be activated by compression, or in another embodiment, can be touch sensitive. In certain embodiments, the switch may require a prolonged depression (e.g., 2 seconds or longer) in order to prevent misfiring of the injector. In other embodiments, the patient sensors can relay a signal to the microcontroller in conjunction with the activation of the inject switch in order for the injection to occur.

Once an injection is initiated, the method 600 includes pushing the pre-filled cartridge forward within the cartridge module with a first drive mechanism, resulting in the protrusion of the needle beyond the lower surface of the injector and through a needle aperture into the subject's skin (block 606). The method 600 further includes applying force to the plunger using a second drive mechanism to expel the medicament through the needle at a controlled rate (block 608). In various arrangements, the motor speed can be actively controlled by the control system through, for example, a closed loop feedback mechanism in order to maintain a smooth flow rate at the specified injection speed. The method 600 can also include sensing an end of a dosage injection (block 610). For example, a photodiode/photoreceptor located at a distal end of the plunger drive mechanism can be disrupted when a lead nut reaches a pre-determined terminal distance, thereby signaling an end of an injection. In such embodiments, the injector may signal to the subject that the injection is complete. The method 600 continues with the retraction of the needle out of the patient and back into the protective housing of the injector (block 612). In some embodiments, a user does not see the needle during the injection process. The door can be released and the pre-filled cartridge can be removed from the injector for disposal. In some embodiments, the pre-filled cartridge deploys an automatic needle-shielding feature within the injector. In other embodiments, the automatic needle-shielding feature is deployed upon lifting the pre-filled cartridge out of the cartridge module. In various embodiments, data related to the injection (average motor speed, injection speed, sensory data such as kinetic temperature profile, cartridge module identification information, injection performance, etc.) can be manually or automatically uploaded wirelessly to a secure database.

Figure 15:
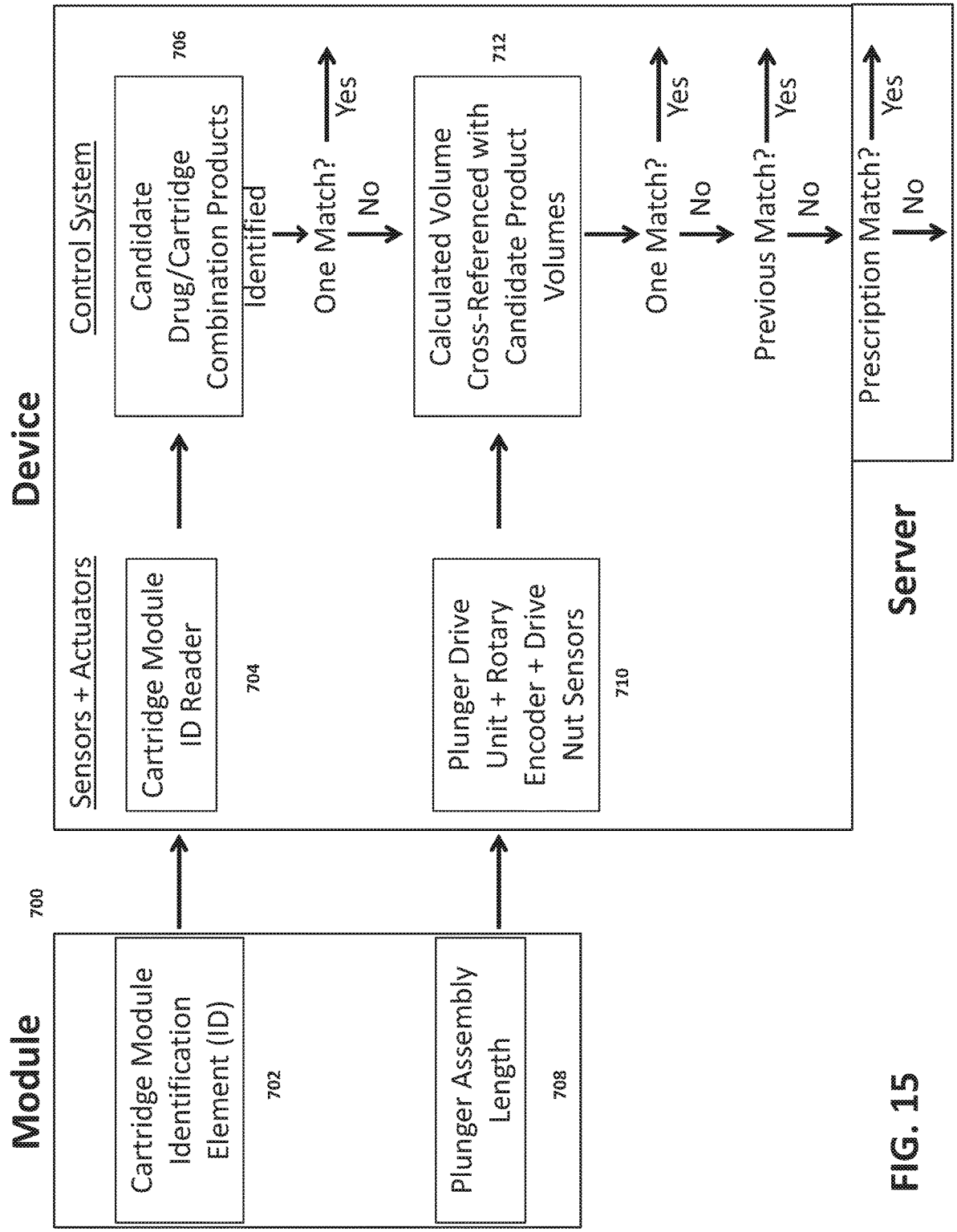
FIG. 15 is a block diagram illustrating a method for automated determination of the identity of the drug/cartridge combination product loaded into the injector, prior to delivery of the medicament by the injector, in accordance with an embodiment of the present technology.

FIG. 15 is a block diagram illustrating a method 700 for automated determination of a medicament dose loaded in the injector prior to delivery of the medicament to the subject in accordance with another embodiment of the present technology. The method 700 begins with identifying information, such as a code or number, stored in the cartridge module identification element (block 702) read by the cartridge module identification code reader (block 704) and communicated to the control system of the injector. The control system refers to a list of known medicaments and doses stored in the pre-filled cartridge associated with the operatively connected cartridge module (block 706). If there is only one medicament dose on the list, then the method is complete and the medicament-specific injection program is executed upon activation of the injector. If there are multiple medicaments or doses on the list, the method continues with the determination of the volume of the dose. For example, a particular cartridge module might be specific for one type of medicament that is prescribed in multiple dosages (e.g. volumes). In this case, the method would continue even though the medicament and corresponding injection program have been identified.

The volume of the dose is determined by measuring the length of the plunger assembly (block 708). This is achieved by extending the plunger drive unit over a linear distance through the plunger housing until the plunger head is engaged. In certain embodiments, engagement of the plunger head is determined by the motor of the plunger drive mechanism stalling at a very low force output. Once the plunger head is engaged, the linear distance traveled by the plunger head is calculated using feedback from the sensors of the plunger drive mechanism (block 710), which can include a rotary encoder for measuring rotational distance, and/or drive nut sensors for measuring linear distance. In certain embodiments, a rotational distance can be used to calculate a linear distance. The distance inputs from the sensors are used by the control system to indirectly calculate the length of the plunger assembly, taking into account the known dimensions of the pre-filled cartridge type (determined by cartridge module identity) and the standard length of the plunger housing from the point of the flange support features where the plunger assembly begins. For example, the plunger housing is 50 mm for every cartridge module, and the operatively connected cartridge module is specific for a standard 1 mL syringe, which has a plunger assembly that extends 40 mm into the plunger housing when full (e.g. a 1 mL dose). If the distance traveled by the plunger drive unit is 30 mm, then the plunger assembly only extends half the maximal distance (e.g. 20 mm) indicating a dosage of 0.5 mL. The control system cross-references the calculated dosage (volume) with the previously mentioned list of medicaments and their sub-lists of know dosages (block 712). If there is only one medicament on the list, then the method is complete and the medicament-specific injection program is executed upon activation of the injector. If there are multiple medicaments on the list, the method continues with the control system accessing a list of at least one previous match stored in the injector memory.

Whenever the method successfully identifies the medicament loaded into the injector, the positive match is stored in the memory for future reference. If there is a previous match that corresponds to the features of the current medicament, such as cartridge module ID or dose volume, then the method is complete and the medicament-specific injection program is executed upon activation of the injector. If the previous match does not correspond to the features of the current medicament, or if there was no previous match, the method continues by wirelessly communicating with a server containing information specific to the injector. In certain embodiments, the medicament prescribed to the patient for delivery using the injector can be stored on a server and be assigned to the injector in possession by the patient. When the server receives a request from an injector assigned to a patient with a known prescription, it can push the identity of the medicament to the device. If there is a prescription that corresponds to the features of the current medicament, such as cartridge module ID or dose volume, then the method is complete and the medicament-specific injection program is executed upon activation of the injector. If the prescription does not correspond to the features of the current medicament, or if there is no prescription on the server, then a generic injection program appropriate for the medicaments associated with the operatively connected cartridge module is executed by the injector.

Figure 16:
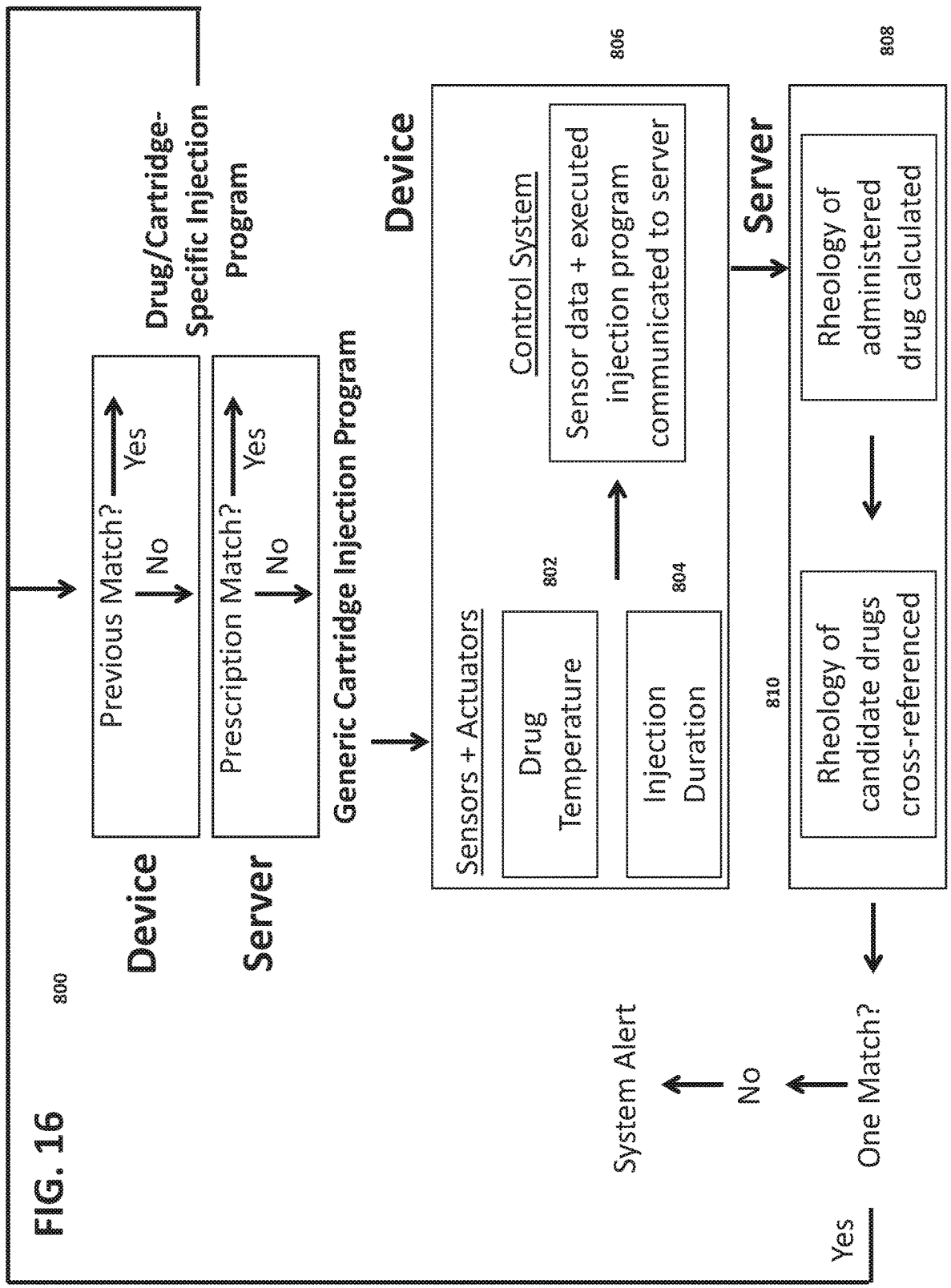
FIG. 16 is a block diagram illustrating a method for automated determination of the identity of the drug/cartridge combination product loaded into the injector, following the delivery of the medicament by the injector, in accordance with an embodiment of the present technology.

FIG. 16 is a block diagram illustrating a method 800 for automated determination of a medicament dose loaded in the injector following the delivery of the medicament to the subject in accordance with another embodiment of the present technology. The method 800 begins with the execution of a generic injection program appropriate for the medicaments associated with the operatively connected cartridge module. The method continues with the collection of sensor data integral to determining the performance of an injection, including the temperature of the drug (block 802) and the duration of the injection (804). The control system organizes the sensor data along with the injection program that was executed and the medicament information that was determined (e.g. cartridge module ID and dose volume), and wirelessly communicates the information to the server (block 806). Algorithms stored on the server use the data received from the injector as inputs to calculate the rheology of the drug administered, including viscosity (block 808). The calculated rheology is then cross-referenced with the rheology values for a list of medicaments that correspond to the medicament information that was determined (e.g. cartridge module ID and dose volume). If there is one medicament that matches the information, the identity is wirelessly communicated to the injector where it is stored as a previous match in the memory of the device, and can be used in the previously mentioned method 700. If there is no match or multiple matches, an alert can be created to draw attention to the injector for a number of reasons. For example, a malfunctioning injector can be replaced or the patient can be contacted in order to determine the identity of the prescribed medicament.

Figure 17:
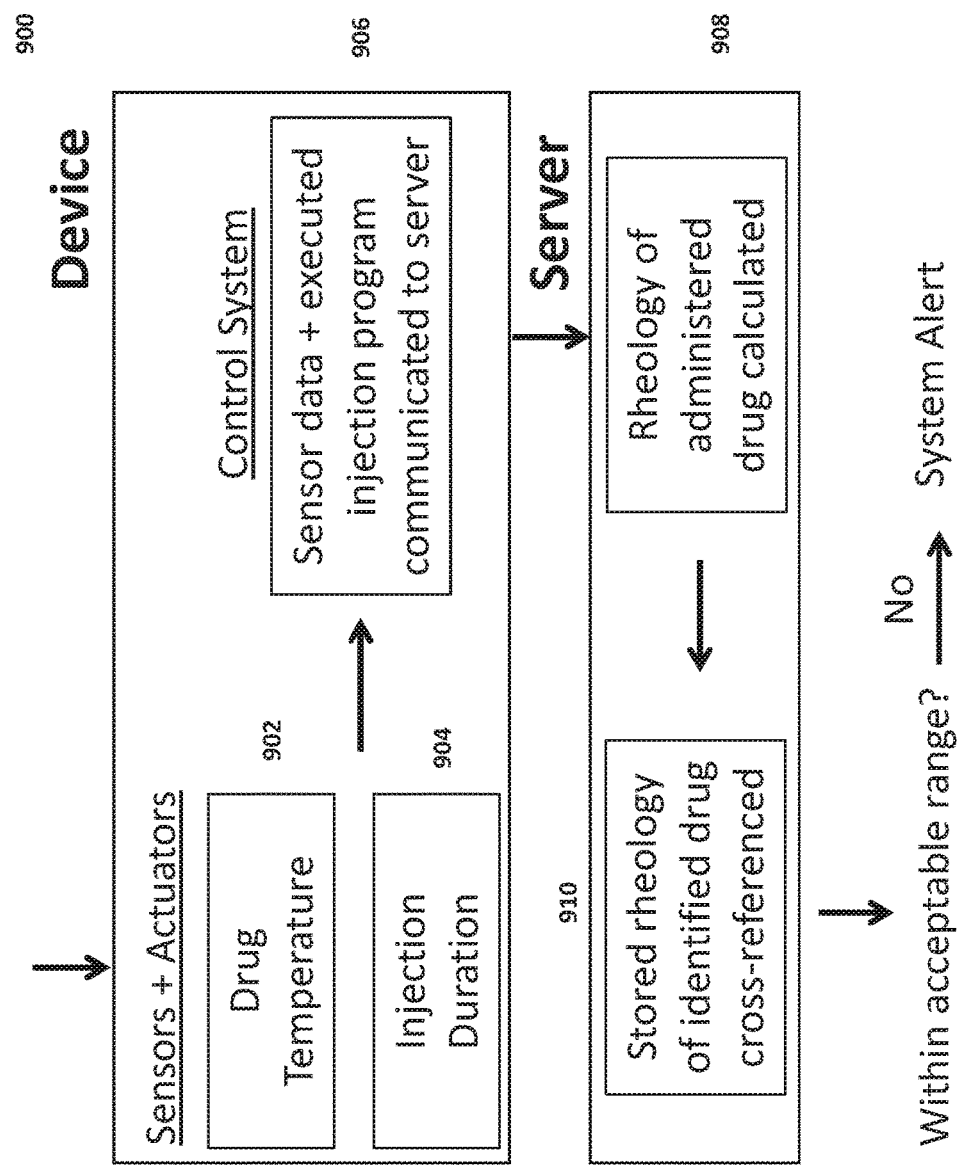
FIG. 17 is a block diagram illustrating a method for automated determination of the quality of an injection, including the physical state of a known medicament as well as the performance on the injector, in accordance with an embodiment of the present technology.

FIG. 17 is a block diagram illustrating a method 900 for automatically determining the quality of an injection, including the physical state of a known medicament as well as the performance of the injector. The method begins following the completion of an injection program specific to a medicament identified according to the method 700 described previously. Sensor data, including drug temperature (block 902) and injection duration (block 904) is communicated to the control system. The control system organizes the sensor data as well as information related to the injection program executed (block 906), and wirelessly transmits the data to a remote server. The server utilizes the data from the injector to calculate the rheology values of the administered drug, such as viscosity (block 908). The method continues with the calculated rheology values cross-referenced to the normal rheology values of the administered drug (block 910). If the calculated and expected rheology values fall outside of an acceptable range of disparity, an alert can be created to draw attention to the injection event for a multitude of reasons. For example, changes to the rheology of a drug can reflect quality issues such as counterfeiting or protein aggregation. All of the data related to the delivered drug and the injection performance is stored on the server long-term for future analysis. For example, analysis of aggregate injection data can identify large-scale quality issues, such as production errors.

In some embodiments, the present disclosure provides a method of administering a medicament to a subject, the method comprising providing an injector assembly to the subject; and providing instructions to the subject for administering the medicament using the injector assembly, wherein the injector assembly is configured to cause a needle to penetrate skin of the subject and thereafter inject an amount of the medicament to the subject through the needle.

In some embodiments, the injector assembly is an injector assembly substantially as described herein.

In some embodiments, the medicament is in a pre-filled cartridge (e.g., a syringe) configured to operably mate with the injector assembly. In some embodiments, the pre-filled cartridge (e.g., syringe) is housed in a cartridge module, wherein the cartridge module operably mates with the injector assembly.

In some embodiments, the instructions include information on how to configure one or more attributes of the injector assembly selected from the group consisting of: injection depth, injection speed, injection amount, or any combination thereof.

In some embodiments, the cartridge module is configured to provide proper injection depth and/or injection amount. In other embodiments, the injection depth and/or the injection amount are associated with an identification code. In some embodiments, the cartridge module includes the identification code.

In some embodiments, the present disclosure provides a method of administering a medicament to a subject, the method comprising providing a cartridge module to the subject; and providing instructions to the subject for administering the medicament using the cartridge module, wherein the cartridge module is configured to removably mate with an injector assembly, the injector assembly configured to cause a needle to penetrate skin of the subject and thereafter inject an amount of the medicament to the subject through the needle.

In some embodiments, the cartridge module is a cartridge module substantially as described herein.

In some embodiments, the injector assembly is an injector assembly substantially as described herein.

In some embodiments, the instructions include information on how to configure one or more attributes of the injector assembly selected from the group consisting of: injection depth, injection speed, injection amount, or any combination thereof. In other embodiments, the cartridge module is configured to provide proper injection depth and/or injection amount. In some embodiments, the injection depth and/or the injection amount are associated with an identification code. In some embodiments, the cartridge module includes the identification code.

In some embodiments, the present disclosure provides a method of administering a medicament to a subject, the method comprising providing a pre-filled cartridge to the subject; and providing instructions to the subject for administering the medicament using the pre-filled cartridge, wherein the pre-filled cartridge includes the medicament and is configured to mate with an injector assembly, the injector assembly configured to cause a needle to penetrate skin of the subject and thereafter inject an amount of the medicament to the subject through the needle.

In some embodiments, the injector assembly is an injector assembly substantially as described herein.

In some embodiments, the instructions include information on how to configure one or more attributes of the injector assembly selected from the group consisting of: injection depth, injection speed, injection amount, or any combination thereof. In other embodiments, the cartridge module is configured to provide proper injection depth and/or injection amount. In some embodiments, the injection depth and/or the injection amount are associated with an identification code. In some embodiments, the cartridge module includes the identification code.

Additional Embodiments

Features of the injection assembly components described above and illustrated in FIGS. 1A-7 can be modified to form additional embodiments configured in accordance with the present technology. The memory and storage devices (e.g., remote databases, remote servers, etc.) are computer-readable media that may store instructions that implement at least portions of the described technology. In various arrangements, the data structures (e.g., memory associated with the injector's internal processor, remote server(s), remote database, etc.) and message structures may be stored or transmitted via a data transmission medium, such as a signal on a communications link. Various communications links may be used, such as the Internet, local area network, a wide area network, etc.

FURTHER EXAMPLES

Example 1. An injector assembly for automatically delivering a dose of a medicament to a subject, the injector assembly comprising: an activation switch for initiating automatic delivery of the dose of the medicament; a needle aperture at a distal end of the injector assembly configured for a needle to pass therethrough; a plunger drive mechanism for applying pressure to a plunger assembly, the plunger drive mechanism including a motor operably connected to the activation switch, and an actuator operably connected to the motor and the plunger assembly; a surface for operatively connecting to at least a portion of a removable cartridge module, the removable cartridge module including: a needle housing for dictating a range of injection depths possible; a plunger housing for aligning the plunger assembly with the plunger drive mechanism; an identification element containing a code associated with a pre-filled cartridge and/or medicament contained within, and a cavity for reversibly securing the pre-filled cartridge; at least one engagement feature for securing the removable cartridge module to the surface.

Example 2. The injector assembly of Example 1, further comprising cartridge drive assembly for moving the pre-filled cartridge axially between the proximal and distal end of the injector assembly, the cartridge drive assembly including at least one gear element operably connected to the motor and the activation switch.

Example 3. The injector assembly of Examples 1 or 2, further comprising an identification reader for reading an identification element containing the code of the cartridge module.

Example 4. The injector assembly of any one of Examples 1 to 3, further comprising a code reader for reading a label of the pre-filled cartridge.

Example 5. The injector assembly of any one of Examples 1 to 4, further comprising at least one sensor.

Example 6. The injector assembly of any one of Examples 1 to 5, further comprising a battery operably connected to the control unit.

Example 7. The injector assembly of any one of Examples 1 to 6, wherein the removable cartridge module includes a top portion integrated with a door.

Example 8. The injector assembly of any one of Examples 1 to 7, wherein the needle aperture is at a distal end of the injector assembly.

Example 9. The injector assembly of Example 5, wherein the injector assembly is configured to prevent activation of the cartridge drive assembly and/or the plunger drive assembly if the sensor does not detect a surface of the subject when the activation switch is pressed.

Example 10. The injector assembly of Example 9, wherein the surface is skin.

Example 11. The injector assembly of Example 5, wherein the injector assembly is configured to stop activation of the cartridge drive assembly and/or the plunger drive assembly if the sensor stops detecting a surface of the subject after the activation switch is pressed.

Example 12. The injector assembly of Example 5, wherein the at least one sensor is a pressure sensor.

Example 13. The injector assembly of Example 5, wherein the at least one sensor is a skin sensor.

Example 14. The injector assembly of any one of Examples 1 to 13, wherein the removable cartridge module further includes a feature conforming to a flange of the pre-filled cartridge.

Example 15. The injector assembly of any one of Examples 1 to 14, wherein upon activation of the activation switch and detection of patient contact by the sensor, the cartridge drive assembly moves the cartridge module a first pre-determined distance towards the distal end of the injector assembly and optionally thereafter moves the cartridge away from the distal end of the injector assembly by at least the first pre-determined distance.

Example 16. The injector assembly of Example 15, wherein the first pre-determined distance is associated with the identification code.

Example 17. The injector assembly of any one of Examples 1 to 16, wherein upon activation of the activation switch, detection of patient contact by the sensor, and movement of the cartridge drive assembly to a first pre-determined distance towards the distal end of the injector, the plunger drive mechanism moves the plunger a second pre-determined distance towards the distal end of the injector assembly.

Example 18. The injector assembly of Example 17, wherein the second pre-determined distance is associated with the identification code.

Example 19. The injector assembly of any one of Examples 1 to 18, wherein a barrel of the pre-filled cartridge includes the medicament in an amount of at least 1 dose.

Example 20. The injector assembly of any one of Examples 1 to 19, wherein a barrel of the pre-filled cartridge includes the medicament in an amount of at least 2 doses, at least 3 doses, at least 4 doses, at least 5 doses, at least 6 doses, at least 7 doses, at least 8 doses, at least 9 doses, at least 10 doses, at least 11 doses, at least 12 doses, at least 13 doses, at least 14 doses, at least 15 doses, at least 16 doses, at least 17 doses, at least 18 doses, at least 19 doses, at least 20 doses, or more than 20 doses.

Example 21. The injector assembly of any one of Examples 1 to 20, further comprising a control system including a microcontroller configured to: store a plurality of identification codes; store a library of injection programs associated with at least one identification code, the injection program comprises at least: a first and/or a second pre-determined distance associated with each identification code, and a pre-determined injection force associated with each identification code; process inputs received from sensors and from the patient; and/or execute an appropriate injection program using inputs from sensors and/or patient Example 22. The injector assembly of Example 21, wherein the control system further comprises a transceiver for receiving data associated with identification codes and injection programs from a server and/or for sending data associated with the performance of an injection, including at least one of: the identification code of the operatively connected cartridge module; the injection program executed; the temperature of the pre-filled cartridge at the time of the injection; the performance of the motor during injection, including motor speed; the duration of time it takes the plunger drive mechanism to move a plunger assembly the second pre-determined distance; and any starts or stops after the initiation of the injection.

Example 23. The injector assembly of Examples 21 or 22, wherein the microcontroller is further configured to cause the cartridge drive assembly to move the cartridge the first pre-determined distance towards and away from the distal end of the injector.

Example 24. The injector assembly of any one of Examples 21-23, wherein the microcontroller is further configured to cause the plunger drive mechanism to move the plunger the second pre-determined distance by exerting a pre-determined injection force on the plunger.

Example 25. The injector assembly of any one of Examples 1 to 24, wherein the activation switch comprises a button, toggle, lever, dial, or rocker.

Example 26. The injector assembly of any one of Examples 1 to 25, wherein the surface has features that form functional connections with corresponding fittings on the removable cartridge module when operatively connected to the cartridge module, the functional connections being configured to: centrally align an internal cavity of the cartridge module with the plunger drive mechanism of the injector assembly; operably mate the cartridge module to the cartridge drive mechanism of the injector assembly; operably mate the electronic components of the cartridge module with the control system of the injector assembly; and/or operably mate the identification element with the identification reader of the injector assembly.

Example 27. The injector assembly of any one of Examples 1 to 26, wherein an operative connection with the removable cartridge module is only formed when the at least one engagement feature securely attaches to at least one fitting of the cartridge module.

Example 28. The injector assembly of any one of Examples 1 to 27, further comprising a display for reporting information and/or instructions to the subject.

Example 29. The injector assembly of any one of Examples 1 to 28, further comprising at least one indicator configured to provide information and/or instruction to the subject.

Example 30. The injector assembly of Example 29, wherein the indicator is selected from the group consisting of a light, a vibration, or a sound.

Example 31. An injector assembly for automatically delivering a dose of a medicament to a subject, the injector assembly comprising: an activation switch for initiating automatic delivery of the dose of the medicament; a needle aperture at a distal end of the injector assembly configured for a needle to pass therethrough; a cavity for housing at least a portion of a removable cartridge module, the removable cartridge module including: a needle housing for dictating the range of injection depths possible, a plunger housing for aligning a plunger assembly with the plunger drive unit, an identification code associated with the pre-filled cartridge and medicament contained within, and a cavity for reversibly securing a pre-filled cartridge, the pre-filled cartridge including: a barrel for containing the medicament and having a proximal end and a distal end, a needle operably connected to the distal end of the barrel, a plunger assembly including a plunger rod having a distal end initially located near the proximal end of the barrel, and a proximal end including a plunger head, and an amount of the medicament, and a plunger drive mechanism for applying pressure to the plunger assembly, the plunger drive mechanism including a motor operably connected to the activation switch, and an actuator operably connected to the motor and the plunger assembly, at least one engagement feature for securing the removable cartridge module in the cavity; a door, at least a portion of which is optionally substantially transparent, for enabling installation and/or removal of the removable cartridge module to/from the cavity; a cartridge drive assembly for moving the cartridge module axially between the proximal and distal end of the injector assembly, the cartridge drive assembly including at least one gear element operably connected to the motor and the activation switch; a code reader for reading the identification code of the cartridge module; an optional code reader for reading the label of the pre-filled cartridge; a patient sensor for detecting contact with skin of the subject; and a battery operably connected to the control unit.

Example 32. The injector assembly of Example 31, wherein the cartridge module includes a top portion integrated with the door.

Example 33. The injector assembly of any one of Examples 31 or 32, wherein the activation switch is at a proximal end.

Example 34. The injector assembly of any one of Examples 31 to 33, wherein the needle aperture is at a distal end.

Example 35. The injector assembly of any one of Examples 31 to 34, wherein the injector assembly is configured to prevent activation of the cartridge drive assembly and/or the plunger drive assembly if the sensor does not detect skin of the subject when the activation switch is pressed.

Example 36. The injector assembly of any one of Examples 31 to 35, wherein the injector assembly is configured to stop activation of the cartridge drive assembly and/or the plunger drive assembly if the sensor stops detecting skin of the subject after the activation switch is pressed.

Example 37. The injector assembly of any one of Examples 31 to 36, wherein the door includes at least one latch.

Example 38. The injector assembly of any one of Examples 31 to 37, wherein the door is rotatably attached to the body of injector assembly by at least one hinge.

Example 39. The injector assembly of any one of Examples 31 to 38, wherein one of the patient sensors is a pressure sensor.

Example 40. The injector assembly of any one of Examples 31 to 39, wherein one of the patient sensors is a skin sensor.

Example 41. The injector assembly of any one of Examples 31 to 40, further comprising a needle shield.

Example 42. The injector assembly of any one of Examples 31 to 41, wherein the removable cartridge module further includes a feature conforming to a flange of the pre-filled cartridge.

Example 43. The injector assembly of any one of Examples 31 to 42, wherein upon activation of the activation switch and detection of patient contact by the sensor, the cartridge drive assembly moves the cartridge module a first pre-determined distance towards the distal end of the injector assembly and optionally thereafter moves the cartridge module away from the distal end of the injector assembly by at least the first pre-determined distance.

Example 44. The injector assembly of any one of Examples 31 to 43, wherein the first pre-determined distance is associated with the identification code.

Example 45. The injector assembly of any one of Examples 31 to 44, wherein upon activation of the activation switch and detection of patient contact by the sensor and the cartridge module moved a first pre-determined distance towards the distal end of the injector, the plunger drive mechanism moves the plunger a second pre-determined distance towards the distal end of the injector assembly.

Example 46. The injector assembly of any one of Examples 31 to 45, wherein the second pre-determined distance is associated with the identification code.

Example 47. The injector assembly of any one of Examples 31 to 46, wherein the barrel includes the medicament in an amount of at least 1 dose.

Example 48. The injector assembly of any one of Examples 31 to 47, wherein the barrel includes the medicament in an amount of at least 2 doses, at least 3 doses, at least 4 doses, at least 5 doses, at least 6 doses, at least 7 doses, at least 8 doses, at least 9 doses, at least 10 doses, at least 11 doses, at least 12 doses, at least 13 doses, at least 14 doses, at least 15 doses, at least 16 doses, at least 17 doses, at least 18 doses, at least 19 doses, at least 20 doses, or more than 20 doses.

Example 49. The injector assembly of any one of Examples 31 to 48, further comprising a control system including a microcontroller configured to: store a plurality of identification codes, and store a library of injection programs each associated with at least one identification code, the injection program containing at least: first and/or second pre-determined distances associated with each identification code, and a pre-determined injection force associated with each identification code, and process inputs received from sensors and from the patient, and execute the appropriate injection program using inputs from sensors and patient.

Example 50. The injector assembly of any one of Examples 31 to 49, wherein the control system further includes a transceiver for receiving data associated with identification codes and injection programs from a server and/or for sending data associated with the performance of an injection, including at least: the identification code of the operatively connected cartridge module, and the injection program executed, and the temperature of the pre-filled cartridge at the time of the injection, and the performance of the motor during injection, including motor speed, and the duration of time it takes the plunger drive mechanism to move a plunger assembly the second pre-determined distance, and any starts or stops after the initiation of the injection.

Example 51. The injector assembly of any one of Examples 31 to 50, wherein the microcontroller is further configured to cause the cartridge drive mechanism to move the cartridge module the first pre-determined distance towards and away from the distal end of the injector.

Example 52. The injector assembly of any one of Examples 31 to 51, wherein the microcontroller is further configured to cause the plunger drive mechanism to move the plunger the second pre-determined distance by exerting a pre-determined injection force on the plunger.

Example 53. The injector assembly of any one of Examples 31 to 52, wherein the switch comprises a button, toggle, lever, dial, or rocker.

Example 54. The injector assembly of any one of Examples 31 to 53, further comprising a spring configured to increase delivery force to the plunger drive mechanism, the spring operably connected to at least a portion of the actuator.

Example 55. A cartridge module comprising: a needle housing for dictating a range of injection depths possible; a plunger housing for aligning a plunger assembly with a plunger drive mechanism; a cavity for reversibly securing a cartridge pre-filled with a medicament; an identification element containing a code associated with a pre-filled cartridge and/or medicament contained within; at least one fitting for removably engaging the cartridge module in an injector assembly; and at least one fitting for operably mating the cartridge module with a cartridge drive assembly, optionally wherein the cartridge drive assembly is integrated with the injector assembly.

Example 56. The cartridge module of Example 55, further comprising at least one fitting for operably mating electronic components with a control system, optionally wherein the control system is integrated with the injector assembly.

Example 57. The cartridge module of any one of Examples 55 or 56, further comprising a shoulder support for mating with a pre-filled cartridge.

Example 58. The cartridge module of any one of Examples 55 to 57, further comprising a flange support for mating with a pre-filled cartridge.

Example 59. The cartridge module of any one of Examples 55 to 58, wherein the shoulder support and/or the flange support are configured to prevent mating with an undesired pre-filled cartridge.

Example 60. The cartridge module of any one of Examples 55 to 59, wherein the cavity includes a barrel housing between shoulder support and flange support, optionally configured to prevent mating with an undesired pre-filled cartridge.

Example 61. The cartridge module of any one of Examples 55 to 60, wherein the needle housing is configured to prevent mating with an undesired pre-filled cartridge.

Example 62. The cartridge module of any one of Examples 55 to 61, wherein the needle housing is configured to align or mate with a needle aperture of an injector device.

Example 63. The cartridge module of any one of Examples 55 to 62, wherein the cavity is centrally aligned with the plunger drive mechanism of an injector device when the fittings are properly engaged with the injector device.

Example 64. The cartridge module of any one of Examples 55 to 63, wherein the identification element is only in communication with a cartridge module identification reader when the fittings are properly engaged with an injector device.

Example 65. The cartridge module of any one of Examples 55 to 64, further comprising a heating element.

Example 66. The cartridge module of any one of Examples 55 to 65, wherein the cartridge module is configured to facilitate different functions based on the identification element.

Example 67. The cartridge module of any one of Examples 55 to 66, wherein the function is selected from the group consisting of recordation of medicament temperature, heating of medicament to a specific temperature, wireless communication with a server, and removal of a cartridge needle cap.

Example 68. A cartridge module comprising: a needle housing for dictating the range of injection depths possible; a plunger housing for aligning a plunger assembly with the plunger drive unit; a cavity for reversibly securing a cartridge pre-filled with a medicament; an identification element containing a code associated with the pre-filled cartridge and medicament contained within; at least one fitting for removably engaging the cartridge module in an injector assembly; and at least one fitting for engaging the cartridge module with a cartridge drive assembly, optionally wherein the cartridge drive assembly is integrated with the injector assembly.

Example 69. The cartridge module of Example 68, including a housing that is open on at least one face and configured to mate with the door of an injection assembly.

Example 70. The cartridge module of any one of Examples 68 or 69, further comprising a shoulder support for mating with a pre-filled cartridge.

Example 71. The cartridge module of any one of Examples 68 to 70, further comprising a flange support for mating with a pre-filled cartridge.

Example 72. The cartridge module of any one of Examples 68 to 71, wherein the shoulder support and/or the flange support are configured to prevent mating with an undesired pre-filled cartridge.

Example 73. The cartridge module of any one of Examples 68 to 72, wherein the cavity includes a barrel housing between shoulder support and flange support, optionally configured to prevent mating with an undesired pre-filled cartridge.

Example 74. The cartridge module of any one of Examples 68 to 73, wherein the needle housing is configured to prevent mating with an undesired pre-filled cartridge.

Example 75. The cartridge module of any one of Examples 68 to 74, wherein the needle housing is configured to align or mate with a needle aperture of an injector device.

Example 76. The cartridge module of any one of Examples 68 to 75, wherein the cartridge module identification element is only in communication with the cartridge module code reader when the fittings are properly engaged with injector device.

Example 77. A method of administering a medicament to a subject, the method comprising: providing an injector assembly to the subject; and providing instructions to the subject for administering the medicament using the injector assembly, wherein: the injector assembly is configured to cause a needle to penetrate skin of the subject and thereafter inject an amount of the medicament to the subject through the needle.

Example 78. The method of Example 77, wherein the injector assembly is as described herein.

Example 79. The method of any one of Examples 77 or 78, wherein the medicament is in a pre-filled syringe configured to operably mate with the injector assembly.

Example 80. The method of any one of Examples 77 to 79, wherein the pre-filled syringe is housed in a cartridge module, wherein the cartridge module operably connects to the injector assembly.

Example 81. The method of any one of Examples 77 to 80, wherein the instructions to the subject comprise information on device status, needle cap status, injection run status, or any combination thereof.

Example 82. The method of any one of Examples 77 to 81, wherein the instructions include information on how to configure one or more attributes of the injector assembly selected from the group consisting of: injection depth, injection speed, injection amount, or any combination thereof.

Example 83. The method of any one of Examples 77 to 82, wherein the cartridge module is configured to provide proper injection depth and/or injection amount.

Example 84. The method of any one of Examples 77 to 83, wherein the injection depth and/or the injection amount are associated with an identification code.

Example 85. The method of any one of Examples 77 to 84, wherein the cartridge module includes the identification code.

Example 86. A method of administering a medicament to a subject, the method comprising: providing a cartridge module to the subject; and providing instructions to the subject for administering the medicament using the cartridge module, wherein the cartridge module is configured to removably mate with an injector assembly, the injector assembly is configured to cause a needle to penetrate skin of the subject and thereafter inject an amount of the medicament to the subject through the needle.

Example 87. The method of Example 86, wherein the cartridge module is the cartridge module as described herein.

Example 88. The method of Example 86, wherein the injector assembly is the injector assembly of as described herein.

Example 89. The method of any one of Examples 86 to 88, wherein the instructions to the subject comprise information on device status, needle cap status, injection run status, or any combination thereof.

Example 90. The method of any one of Examples 86 to 89, wherein the instructions include information on how to configure one or more attributes of the injector assembly selected from the group consisting of: injection depth, injection speed, injection amount, or any combination thereof.

Example 91. The method of any one of Examples 86 to 90, wherein the cartridge module is configured to provide proper injection depth and/or injection amount.

Example 92. The method of any one of Examples 86 to 91, wherein the injection depth and/or the injection amount are associated with an identification code.

Example 93. The method of any one of Examples 86 to 92, wherein the cartridge module includes the identification code.

Example 94. A method of administering a medicament to a subject, the method comprising: providing a pre-filled cartridge to the subject; and providing instructions to the subject for administering the medicament using the pre-filled cartridge, wherein the pre-filled cartridge includes the medicament and is configured to mate with a cartridge module removably and operatively connected to the injector assembly, the injector assembly configured to cause a needle to penetrate skin of the subject and thereafter inject an amount of the medicament to the subject through the needle.

Example 95. The method of Example 94, wherein the injector assembly is the injector assembly as described herein.

Example 96. The method of any one of Examples 94 or 95, wherein the instructions to the subject comprise information on device status, needle cap status, injection run status, or any combination thereof.

Example 97. The method of any one of Examples 94 to 96, wherein the instructions include information on how to configure one or more attributes of the injector assembly selected from the group consisting of: injection depth, injection speed, injection amount, or any combination thereof.

Example 98. The method of any one of Examples 94 to 97, wherein the cartridge module is configured to provide proper injection depth and/or injection amount.

Example 99. The method of any one of Examples 94 to 98, wherein the injection depth and/or the injection amount are associated with an identification code.

Example 100. The method of any one of Examples 94 to 99, wherein the cartridge module includes the identification code.

I claim:

1. A system for automatically delivering a dose of a medicament to a subject, the system comprising:
    a plurality of removable cartridge modules, wherein each removable cartridge module of the plurality of removable cartridge modules comprises:
        a needle housing configured to dictate a range of injection depths possible,
        a plunger housing configured to align a plunger assembly with a plunger drive mechanism,
        at least one fitting configured to connect the removable cartridge module to an injector assembly, wherein the at least one fitting is shaped identically in each removable cartridge module of the plurality of removable cartridge modules,
        an identification element comprising an identification code associated with a pre-filled cartridge and/or medicament contained within, and
        a cavity configured to reversibly secure the pre-filled cartridge; and
    the injector assembly comprising:
        an activation switch configured to initiate automatic delivery of the dose of the medicament;
        a needle aperture at a distal end of the injector assembly configured for a needle to pass therethrough;
        the plunger drive mechanism configured to apply pressure to the plunger assembly, the plunger drive mechanism comprising a motor operably connected to the activation switch, a rotary encoder to measure an amount of the pressure, and an actuator operably connected to the motor and the plunger assembly;
        a surface configured to operatively connect to at least a portion of one removable cartridge module of the plurality of removable cartridge modules;
        at least one engagement feature configured to securely engage the removable cartridge module to the surface via the corresponding at least one fitting; and
        a cartridge drive assembly configured to move the pre-filled cartridge axially between a proximal and a distal end of the injector assembly, the cartridge drive assembly comprising at least one gear element operably connected to the motor and the activation switch.

2. The injector assembly of claim 1, further comprising an identification reader configured to read the identification element comprising the identification code of the cartridge module.

3. The injector assembly of claim 1, further comprising at least one sensor, wherein the injector assembly is configured to prevent activation of the cartridge drive assembly and/or the plunger drive mechanism when the sensor does not detect a surface of the subject when the activation switch is pressed.

4. The injector assembly of claim 3, wherein:
the injector assembly is configured to stop activation of the cartridge drive assembly and/or the plunger drive mechanism when the sensor stops detecting a surface of the subject after the activation switch is pressed, and the at least one sensor is a pressure sensor or a skin sensor.

5. The injector assembly of claim 1, wherein upon activation of the activation switch and detection of patient contact by a sensor, the cartridge drive assembly is configured to move the cartridge module a first pre-determined distance towards the distal end of the injector assembly and optionally configured to move the cartridge module away from the distal end of the injector assembly by at least the first pre-determined distance after the cartridge module is moved toward the distal end.

6. The injector assembly of claim 5, wherein the first pre-determined distance is associated with the identification code.

7. The injector assembly of claim 1, wherein upon activation of the activation switch, detection of patient contact by a sensor, and movement of the cartridge drive assembly to a first pre-determined distance towards the distal end of the injector, the plunger drive mechanism is configured to move the plunger a second pre-determined distance towards the distal end of the injector assembly.

8. The injector assembly of claim 7, wherein the second pre-determined distance is associated with the identification code.

9. The injector assembly of claim 1, wherein a barrel of the pre-filled cartridge contains the medicament in an amount of at least 2 doses, at least 3 doses, at least 4 doses, at least 5 doses, at least 6 doses, at least 7 doses, at least 8 doses, at least 9 doses, at least 10 doses, at least 11 doses, at least 12 doses, at least 13 doses, at least 14 doses, at least 15 doses, at least 16 doses, at least 17 doses, at least 18 doses, at least 19 doses, at least 20 doses, or more than 20 doses.

10. The injector assembly of claim 1, further comprising a control system comprising a microcontroller configured to:
access a plurality of identification codes;
access a library of injection programs associated with at least one identification code of the plurality of identification codes, the injection program comprises at least:
a first and/or a second pre-determined distance associated with each identification code of the plurality of identification codes, and
a pre-determined injection force associated with each identification code of the plurality of identification codes;
process inputs received from sensors and from a patient; and/or
execute an appropriate injection program using inputs from the sensors and/or patient.

11. The injector assembly of claim 10, wherein the control system further comprises a transceiver configured to receive data associated with identification codes and injection programs from a server and/or configured to send data associated with the performance of an injection, the data associated with the identification codes and the data associated with the performance of the injection comprising at least one of:
the identification code of the operatively connected cartridge module;
the injection program executed;
the temperature of the pre-filled cartridge at the time of the injection;
the performance of the motor during injection, including motor speed;
the duration of time it takes the plunger drive mechanism to move a plunger assembly the second pre-determined distance; and
any starts or stops after the initiation of the injection.

12. The injector assembly of claim 10, wherein the microcontroller is further configured to:
cause the cartridge drive assembly to move the cartridge the first pre-determined distance towards and away from the distal end of the injector or
cause the plunger drive mechanism to move the plunger the second pre-determined distance by exerting a pre-determined injection force on the plunger.

* * * * *